(12) United States Patent
Al-Ali

(10) Patent No.: US 10,292,664 B2
(45) Date of Patent: May 21, 2019

(54) MONITOR CONFIGURATION SYSTEM

(71) Applicant: MASIMO CORPORATION, Irvine, CA (US)

(72) Inventor: Ammar Al-Ali, San Juan Capistrano, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 15/224,085

(22) Filed: Jul. 29, 2016

(65) Prior Publication Data

US 2016/0331332 A1 Nov. 17, 2016

Related U.S. Application Data

(63) Continuation of application No. 12/430,742, filed on Apr. 27, 2009, now abandoned.
(Continued)

(51) Int. Cl.
*A61B 5/02* (2006.01)
*A61B 5/00* (2006.01)
(Continued)

(52) U.S. Cl.
CPC .......... *A61B 5/7445* (2013.01); *A61B 5/002* (2013.01); *A61B 5/0261* (2013.01); *A61B 5/02438* (2013.01); *A61B 5/14546* (2013.01); *A61B 5/14551* (2013.01); *A61B 5/14552* (2013.01); *A61B 5/6826* (2013.01);
(Continued)

(58) Field of Classification Search
CPC .......... A61B 5/00; A61B 5/024; A61B 5/145; A61B 5/1455; A61B 5/02438; A61B 5/0261; A61B 5/14551; A61B 5/6826; A61B 5/6838; A61B 5/002; A61B 5/14546; A61B 5/7475; A61B 5/7445; A61B 5/743; A61B 5/14552; A61B 5/7495;
(Continued)

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

JP 2006-254964 A 9/2006

OTHER PUBLICATIONS

US 8,845,543 B2, 09/2014, Diab et al. (withdrawn)
(Continued)

*Primary Examiner* — Eric J Messersmith
(74) *Attorney, Agent, or Firm* — Knobbe Martens Olson & Bear, LLP

(57) ABSTRACT

A monitor configuration system which communicates with a physiological sensor, the monitor configuration system including one or more processors and an instrument manager module running on the one or more processors. At least one of the one or more processors communicates with the sensor and calculates at least one physiological parameters responsive to the sensor. The instrument manager controls the calculation, display and/or alarms based upon the physiological parameters. A configuration indicator identifies the configuration profile. In one aspect of the invention, the physiological sensor is a optical sensor that includes at least one light emitting diode and at least one detector.

8 Claims, 19 Drawing Sheets

Related U.S. Application Data

(60) Provisional application No. 61/050,205, filed on May 3, 2008, provisional application No. 61/126,268, filed on May 2, 2008.

(51) Int. Cl.
  *A61B 5/024* (2006.01)
  *A61B 5/026* (2006.01)
  *A61B 5/1455* (2006.01)
  *A61B 5/145* (2006.01)

(52) U.S. Cl.
  CPC ............ *A61B 5/6838* (2013.01); *A61B 5/743* (2013.01); *A61B 5/7475* (2013.01); *A61B 5/7495* (2013.01); *A61B 5/746* (2013.01); *A61B 2560/0271* (2013.01); *A61B 2560/0276* (2013.01); *A61B 2560/0443* (2013.01); *A61B 2562/227* (2013.01)

(58) Field of Classification Search
  CPC .... A61B 2560/0276; A61B 2560/0443; A61B 5/746; A61B 2562/227; A61B 2560/0271
  See application file for complete search history.

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,106,460 A | 8/2000 | Panescu et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,221,012 B1 | 4/2001 | Maschke et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,960 B1 | 7/2001 | Ahne et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,394,346 B1 | 5/2002 | Bonneau et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,475,146 B1 | 11/2002 | Frelburger et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |

(56) References Cited

U.S. PATENT DOCUMENTS

| | | |
|---|---|---|
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,762,930 B2 | 7/2004 | Minne |
| 6,770,028 B1 | 8/2004 | Ali et al. |
| 6,771,994 B2 | 8/2004 | Kiani et al. |
| 6,790,178 B1 | 9/2004 | Mault |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,225,809 B1 | 6/2007 | Bowen et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| 7,343,439 B2 | 3/2008 | Mills et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,485,499 B2 | 2/2009 | Brewer et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,706,896 B2 | 4/2010 | Music et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |

(56) References Cited

U.S. PATENT DOCUMENTS

| | | |
|---|---|---|
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |

(56) References Cited

U.S. PATENT DOCUMENTS

| | | |
|---|---|---|
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Ai-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |

(56) References Cited

U.S. PATENT DOCUMENTS

| | | |
|---|---|---|
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 2003/0002562 A1 | 1/2003 | Yerlikaya et al. |
| 2003/0130590 A1* | 7/2003 | Bui ............... A61B 5/0002 600/537 |
| 2006/0220881 A1* | 10/2006 | Al-Ali ........... A61B 5/14552 340/573.1 |
| 2006/0229558 A1 | 10/2006 | Heston et al. |
| 2006/0265186 A1* | 11/2006 | Holland ......... G06F 19/3468 702/182 |
| 2007/0064419 A1* | 3/2007 | Gandhi ......... H05B 33/0857 362/231 |
| 2007/0282478 A1 | 12/2007 | Al-Ali et al. |
| 2008/0014829 A1 | 1/2008 | Dyer et al. |
| 2008/0041380 A1 | 2/2008 | Wallace et al. |
| 2008/0156871 A1 | 7/2008 | Fidalgo et al. |
| 2008/0232605 A1* | 9/2008 | Bagha ............... A61B 7/04 381/67 |
| 2009/0062664 A1 | 3/2009 | Chang et al. |
| 2009/0171175 A1 | 7/2009 | Li et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2011/0082711 A1 | 4/2011 | Poeze et al. |
| 2011/0087083 A1 | 4/2011 | Poeze et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237969 A1 | 9/2011 | Eckerbom et al. |
| 2011/0288383 A1 | 11/2011 | Diab |
| 2011/0301444 A1 | 12/2011 | Al-Ali |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0190581 A1 | 7/2013 | Al-Ali et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0303520 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |

(56) References Cited

U.S. PATENT DOCUMENTS

| | | |
|---|---|---|
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0336481 A1 | 11/2014 | Shakespeare et al. |
| 2014/0357966 A1 | 12/2014 | Al-Ali et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014084 A1 | 1/2017 | Al-Ali et al. |
| 2017/0021099 A1 | 1/2017 | Al-Ali et al. |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |

(56) References Cited

U.S. PATENT DOCUMENTS

| | | |
|---|---|---|
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192953 A1 | 7/2018 | Shreim et al. |
| 2018/0199871 A1 | 7/2018 | Pauley et al. |
| 2018/0214090 A1 | 8/2018 | Al-Ali et al. |
| 2018/0218792 A1 | 8/2018 | Muhsin et al. |

OTHER PUBLICATIONS

US 9,579,050 B2, 02/2017, Al-Ali (withdrawn)
International Search Report and Written Opinion in related Application No. PCT/US2009/041838 dated Aug. 4, 2009, in 16 pages.

\* cited by examiner

MONITOR CONFIGURATION SYSTEM

CROSS-REFERENCE TO RELATED APPLICATIONS

The present application is a continuation of U.S. patent application Ser. No. 12/430,742, filed Apr. 27, 2009, titled Monitor Configuration System, which claims priority benefit under 35 U.S.C. § 119(e) to U.S. Provisional Patent Application Ser. No. 61/126,268, filed May 2, 2008, titled Monitor User Interface; and U.S. Provisional Patent Application Ser. No. 61/050,205 filed May 3, 2008, titled Monitor Configuration System. All of the above cited provisional applications are hereby incorporated by reference herein.

BACKGROUND OF THE INVENTION

Pulse oximetry systems for measuring constituents of circulating blood have gained rapid acceptance in a wide variety of medical applications including surgical wards, intensive care and neonatal units, general wards, home care, physical training, and virtually all types of monitoring scenarios. A pulse oximetry system generally includes an optical sensor applied to a patient, a monitor for processing sensor signals and displaying results and a patient cable electrically interconnecting the sensor and the monitor. A pulse oximetry sensor has light emitting diodes (LEDs), typically one emitting a red wavelength and one emitting an infrared (IR) wavelength, and a photodiode detector. The emitters and detector are attached to a patient tissue site, such as a finger. The patient cable transmits drive signals to these emitters from the monitor, and the emitters respond to the drive signals to transmit light into the tissue site. The detector generates a signal responsive to the emitted light after attenuation by pulsatile blood flow within the tissue site. The patient cable transmits the detector signal to the monitor, which processes the signal to provide a numerical readout of physiological parameters such as oxygen saturation ($SpO_2$) and pulse rate. Advanced physiological monitoring systems utilize multiple wavelength sensors and multiple parameter monitors to provide enhanced measurement capabilities including, for example, the measurement of carboxyhemoglobin (HbCO), methemoglobin (HbMet) and total hemoglobin (Hbt).

Pulse oximeters capable of reading through motion induced noise are disclosed in at least U.S. Pat. Nos. 6,770,028, 6,658,276, 6,650,917, 6,157,850, 6,002,952, 5,769,785, and 5,758,644; low noise pulse oximetry sensors are disclosed in at least U.S. Pat. Nos. 6,088,607 and 5,782,757; all of which are assigned to Masimo Corporation, Irvine, Calif. ("Masimo") and are incorporated by reference herein.

Physiological monitors and corresponding multiple wavelength optical sensors are described in at least U.S. patent application Ser. No. 11/367,013, filed Mar. 1, 2006 and titled Multiple Wavelength Sensor Emitters and U.S. patent application Ser. No. 11/366,208, filed Mar. 1, 2006 and titled Noninvasive Multi-Parameter Patient Monitor, both assigned to Masimo Laboratories, Irvine, Calif. ("Masimo Labs") and both incorporated by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-5™, Rad-5v™ or PPO+™ Masimo SET® pulse oximeters, are all available from Masimo. Physiological monitoring systems including multiple wavelength sensors and corresponding noninvasive blood parameter monitors, such as Rainbow™ adhesive and reusable sensors and Rad-57™, Rad-87™ and Radical-7™ monitors for measuring $SpO_2$, pulse rate, perfusion index, signal quality, HbCO and HbMet among other parameters are also available from Masimo.

SUMMARY OF THE INVENTION

Advanced noninvasive physiological parameter monitors provide medical practitioners with substantial operational flexibility, including the ability to set parameters displayed, display format, alarm thresholds, alarm types, sensitivity and averaging times, to name just a few. Optimal settings vary with the monitoring application. Monitoring in a hospital environment may differ from that of an ambulance or out-patient clinic. Also different hospital wards servicing different types of patients with different medical care needs are likely to require different monitor settings. For example, ER monitoring requirements will likely differ from those of a surgical ward. Monitoring of neonatal patients will likely differ from monitoring of geriatric patients. Thus, the operational flexibility of these monitors is a challenge to medical staff and administrators at various facilities, especially if a monitor is used for multiple purposes and patient types or if monitors are frequently moved between locations within a large facility.

A monitor configuration system meets this challenge in various respects. In an embodiment, a monitor configuration system advantageously provides a readily recognizable indication of the current default settings. This indication can be associated with a particular ward or patient group, as examples. In addition, a monitor can be programmed with any of multiple user-defined default settings, each associated with a unique configuration indication. In an embodiment, the monitor control panel and display provide hidden menus that allow technical support staff to quickly change configuration profiles to best suit the current monitor usage without risk of accidental configuration changes by medical staff. Also, technical staff can utilize manual procedures or programming aids to conveniently enter or modify one or more default settings.

Advantageously, an aspect of a monitor configuration system allows users to change to default settings using front-panel keys or an external configuration application. This user-defined "configuration profile" overrides the factory default settings and is retained after a power cycle. A user may also associate a color and/or a display message with the profile, as a "configuration indicator," which allows a user to verify at a glance which configuration profile is the default. In an embodiment, a front-panel colored light is a configuration indicator. If changes are made to the device settings after the configuration profile feature has been enabled, the front panel light will turn off, indicating a change from the saved profile settings. In other embodiments a colored plug-in memory, dongle or similar device programs the monitor settings and serves as a profile indicator.

One aspect of a monitor configuration system communicates with a physiological sensor and includes a processor, for example, a digital signal processor (DSP) and an instrument manager processor. The physiological sensor can have emitters that transmit optical radiation into a tissue site and at least one detector that receives the optical radiation after attenuation by pulsatile blood flow within the tissue site. The DSP can communicate with the sensor and calculate physiological parameters responsive to the sensor. An instrument manager receives the calculated physiological parameters from the DSP, transmits the physiological parameters to a display and controls alarms based upon the physiological parameters. The instrument manager is responsive to a configuration profile that specifies DSP calculations, physiological parameter displays and alarms. The configuration indicator identifies the configuration profile. In various embodiments, the configuration indicator comprises a panel light. The instrument manager selects between a factory-default configuration profile and a user-specified configuration profile. The panel light displays a first color when the factory-default settings are selected and a second color when the user-specified settings are selected. The user-specified settings are manually defined. The panel light color for user-specified settings is manually defined. The configuration indicator comprises a top-mounted alphanumeric display.

Another aspect of a monitor configuration system comprises a sensor having emitters that transmit optical radiation into a tissue site and at least one detector that receives the optical radiation after attenuation by pulsatile blood flow within the tissue site. A calculator communicates with the sensor and calculates physiological parameters responsive to the sensor. An instrument manager receives the calculated physiological parameters from the calculator, transmits the physiological parameters to a display and controls alarms based upon the physiological parameters. The instrument manager is responsive to a configuration profile with respect to calculator calculations, physiological parameter displays and alarms. In various embodiments the instrument manager reads the configuration profile via the I/O port. A memory device stores the configuration profile and is removably attached to the I/O port so as to communicate the configuration profile to the instrument manager. A color is affixed to at least a portion of the memory device. The color corresponds to the configuration profile. The memory device and its color are readily visible to a monitor user when the memory device is removably attached to the I/O port so as to designate the configuration profile to the user. A configuration profile routine executes on the instrument manager and writes the memory device with configuration profile settings.

A further aspect of a monitor configuration system comprises a configuration profile of user-specified settings defined for a physiological monitor. The configuration profile is selected to override corresponding factory-specified settings. A color is associated with the configuration profile. The selected profile is indicated by displaying the associated color. The user-specified settings and the factory-specified settings each relate to at least one of calculating physiological parameters, displaying the physiological parameters and alarming based upon the physiological parameters. In various embodiments, the configuration profile is defined by reading the configuration profile into the physiological monitor. The selected profile is indicated by illuminating a portion of the physiological monitor with the color. The reading comprises downloading the configuration profile from an input/output (I/O) port. The illuminating comprises activating a colored panel light on the monitor. The selecting comprises receiving from a wireless device a code corresponding to the configuration profile and activating the configuration profile according to the code.

An additional aspect of a monitor configuration system comprises a profile definition means for setting parameter measurement, display and alarm characteristics of a physiological monitor, a profile selection means for activating a defined profile and a profile indication means for cuing a monitor user as to the selected profile. In various embodiments the profile definition means comprises a menu means for manually entering profile settings. The profile selection means comprises a save means for specifying a defined profile as the monitor default settings. The profile indication means comprises a color selection means for associating a color with a saved profile and an illumination means for displaying the color. The profile definition means comprises a downloading means for transferring profile settings to the monitor via at least one of an I/O port and a docking port. The profile selection means comprises a wireless means for specifying a defined profile as the monitor default settings.

BRIEF DESCRIPTION OF THE DRAWINGS

FIGS. 1-5E are perspective views of physiological monitors utilizing various monitor configuration system embodiments;

FIG. 1 is a standalone physiological monitor having a front-panel colored light and a top-mounted display as configuration indicators;

FIG. 2 is a standalone physiological monitor having a color-coded plug-in configuration indicator;

FIG. 3 is a removable handheld monitor having a front-panel colored light and a corresponding docking station having a top-mounted display configuration indicator;

FIG. 4 is a physiological monitoring system and a corresponding plug-in module having a colored panel light and a colored monitor display as configuration indicators;

FIGS. 5A-E is a physiological monitoring system including a removable satellite module, a docking handheld monitor and plug-ins each having configuration indicators;

DETAILED DESCRIPTION OF THE PREFERRED EMBODIMENTS

Figure 1:
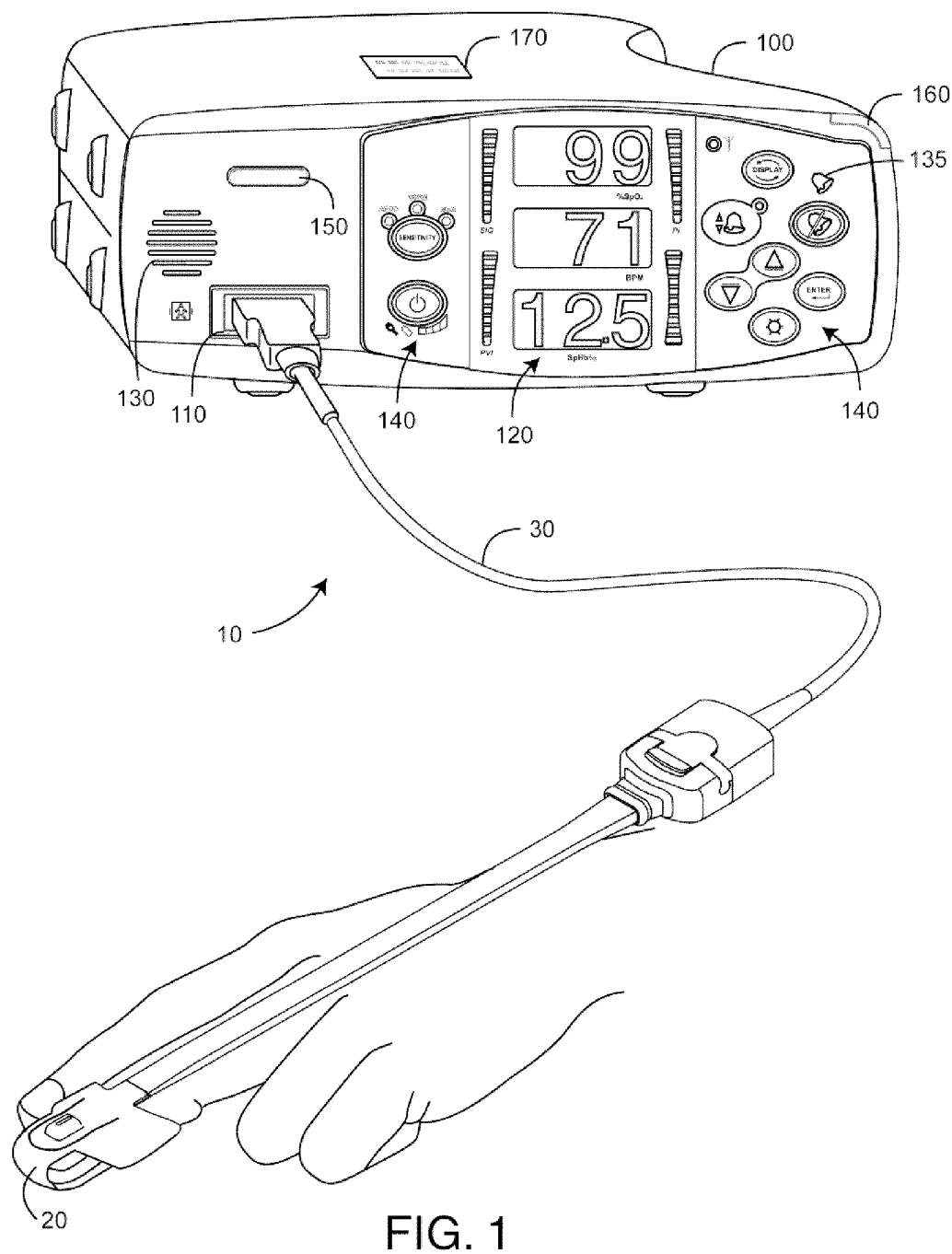

FIG. 1 illustrates a physiological measurement system 10 that utilizes a configuration indicator embodiment. The physiological measurement system 10 has monitor 10 and a multiple wavelength optical sensor 20. The sensor 20 allows the measurement of various blood constituents and related parameters. The sensor 20 is configured to communicate with a monitor sensor port 110 via a patient cable 30. The sensor 20 is typically attached to a tissue site, such as a finger. The patient cable 30 transmits a drive signal from the monitor 100 to the sensor 20 and a resulting detector signal from the sensor 20 to the monitor 100. The monitor 100 processes the detector signal to provide a numerical readout of measured blood parameters including oxygen saturation (SpO$_2$), pulse rate (PR), carboxyhemoglobin (HbCO), methemoglobin (HbMet) and total hemoglobin (Hbt), to name a few. Displays 120 provide readouts, bar graphs or other visual presentations of the measured parameters. A speaker 130 or other audio transducer generates beeps, alarms or other audio presentations of the measured parameters. Monitor keys (buttons) 140 provide control over operating modes and alarms, to name a few. A system status light 160 indicates alarm status, data status and monitor mode.

As described in detail below, a user can determine the operational characteristics of the monitor 100 by changing various factory default settings. A particular group of custom settings, described herein as a configuration profile, determines the physiological parameters that are measured, various options related to those measurements, how the physiological parameters are displayed, alarm thresholds for the physiological parameters and alarm types, to name a few. Many configuration profiles are possible for a monitor, and some profiles are more appropriate for a particular healthcare application or environment than others. A configuration indicator advantageously allows a user to quickly recognize that a particular configuration profile is the current default setting for that monitor.

As shown in FIG. 1, a panel light 150 displays a selected one of various colors, such as shown in TABLE 1. Advantageously, each color of the panel light 150 can be associated with a unique configuration profile. Accordingly, medical staff using the monitor can readily recognize and discern the monitor's settings by observing the illumination color. As an example, pink can be associated with standardized ER settings, teal with surgical ward settings and blue with general ward settings.

The panel light 150 illuminates with a color associated with a user-defined profile at power on. In one embodiment, the panel light 150 glows and slowly cycles from bright to dim if a temporary change has been made to the user-defined profile or if defaults have been activated via the control buttons 140. The panel light 150 returns to a solid state when settings are returned to the user-defined profile. In an embodiment, a factory default profile is associated with purple having RGB values of R 75, G 40 and B 55. In an embodiment, optional profile colors for user defined profiles are represented by the RGB codes listed in TABLE 1, below.

TABLE 1

Colors and RGB Values

| COLOR DESCRIPTION | RGB CODE |
| --- | --- |
| Dark Purple | 10 05 15 |
| Electric Blue | 25 65 40 |
| Teal | 15 65 15 |
| Green | 10 40 05 |
| Pink | 95 20 15 |
| Light Pink | 60 20 05 |

Further shown in FIG. 1, a top-mounted display 170, such as an LCD mini-screen, displays radio communication status, system status and, in an embodiment, a textual description of the current profile corresponding to the panel light 150. This allows medical staff to verify the profile associated with a particular panel light color. For example, the display 170 might indicate "ER," "surgical," or "general" corresponding to selected profiles for those wards. The monitor illustrated in FIG. 1 is described in further detail with respect to FIGS. 12A-D, below.

Figure 2:
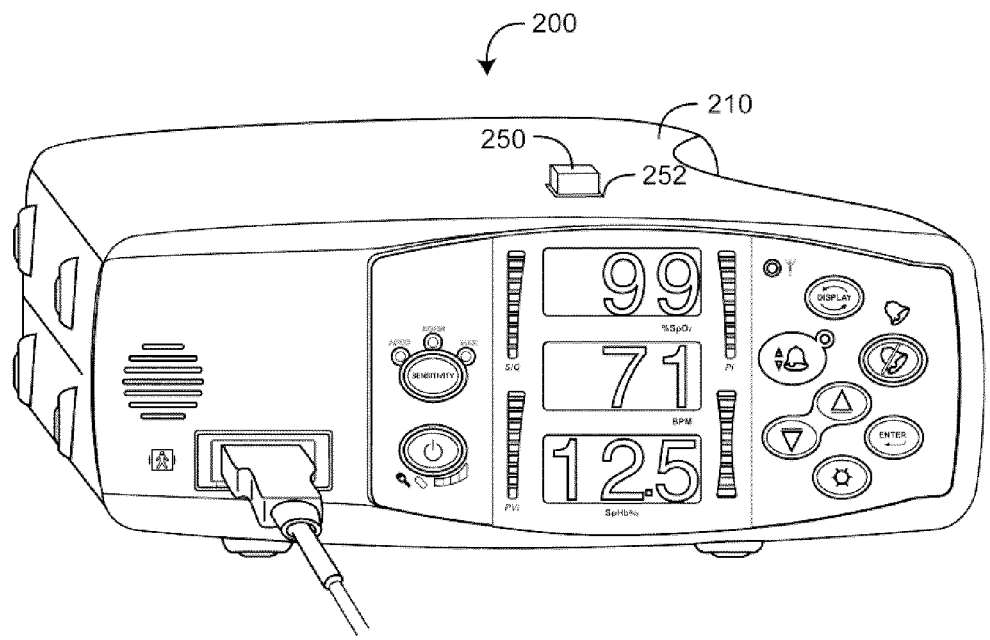

FIG. 2 illustrates a physiological measurement system 200 that utilizes a plug-in configuration indicator. In particular, a color-coded memory device 250 is removably plugged into a configuration port 252. The memory 250 is preloaded with a specific configuration profile, and the monitor 210 reads the memory 250 so as to transfer the corresponding settings into the monitor. Different color-coded memories may store different configuration profiles, i.e. user-selected monitor settings. A user can advantageously select a memory by color and plug the memory 250 into the configuration port 252 so as to quickly customize the monitor 210 for a particular medical application or healthcare environment. For example, red may represent a hospital emergency room (ER), yellow a surgical ward and green a general care ward. Accordingly, red, yellow and green-coded memories are loaded with monitor settings appropriate to the ER, surgical ward and general ward, respectively. A healthcare provider using the monitor 210 can then quickly determine if the monitor is configured appropriately for their purpose. Thus, the memory 250 serves both as a configuration defining device and as a configuration indicator. In other embodiments, color-coded dongles each having a memory, standard connectors and corresponding standard interface electronics can be plugged into a standardized monitor port, such as USB or RS-232. In an embodiment, color coded buttons are provided instead of, or in addition to the memories or dongles discussed above. The color coded buttons allow a user to quickly select a desired configuration. In an embodiment, a color coordinated or non-color coordinated light is provided on or next to each button, memory or dongle. The light corresponding to the selected profile is lit.

Figure 3:
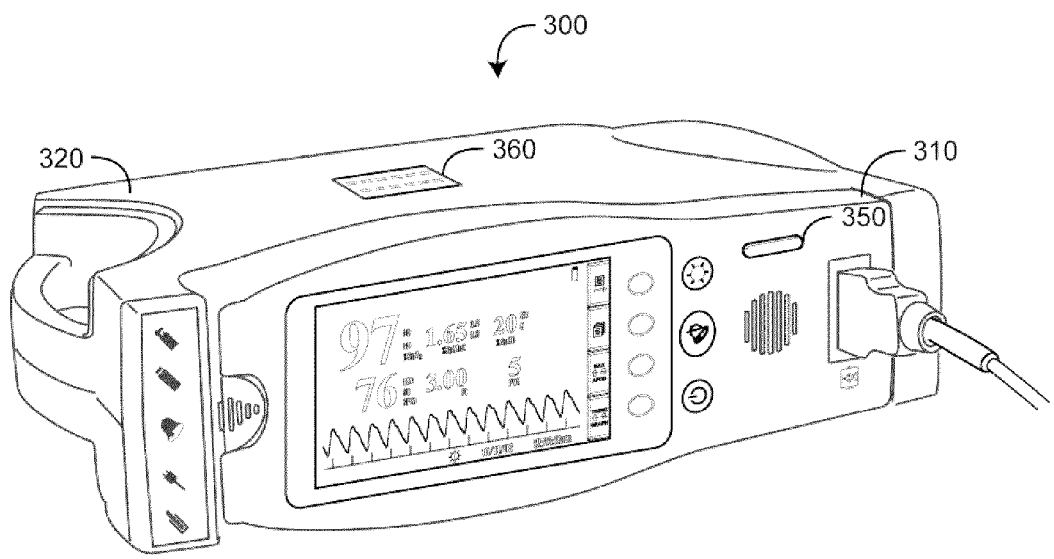

FIG. 3 illustrates a physiological measurement system 300 having a removable handheld monitor 310 and a corresponding docking station 320. The docking station 320 may range in complexity from a simple charging station to an independent physiological measurement system that enhances the capabilities of the handheld when docked. For example, a docking station embodiment may upgrade the capabilities of other monitors, such as described in U.S. Pat. No. 6,584,336 titled Universal/Upgrading Pulse Oximeter, issued Jun. 24, 2003, assigned to Masimo and incorporated by reference herein. A panel light 350 on the handheld 310 displays a selected color associated with a handheld configuration profile, such as described with respect to FIG. 1, above. A top-mounted display 360 on the docking station also provides a textual description of a current profile. In an embodiment, the display 360 simply provides a textual description of the handheld configuration profile when docked. In an embodiment, the display 360 indicates a pre-programmed docking station profile that is adopted by the handheld when docked, modifying the panel light 350 accordingly. In an embodiment, the docking station profile is combined with the handheld profile when docked, modifying both the panel light 350 and the display 360 accordingly. In an embodiment, the docking station profile is downloaded to the handheld 310 when docked, as verified by the handheld panel light 350. In this manner, the docking station 320 functions as a profile defining device for the handheld 310.

Figure 4:
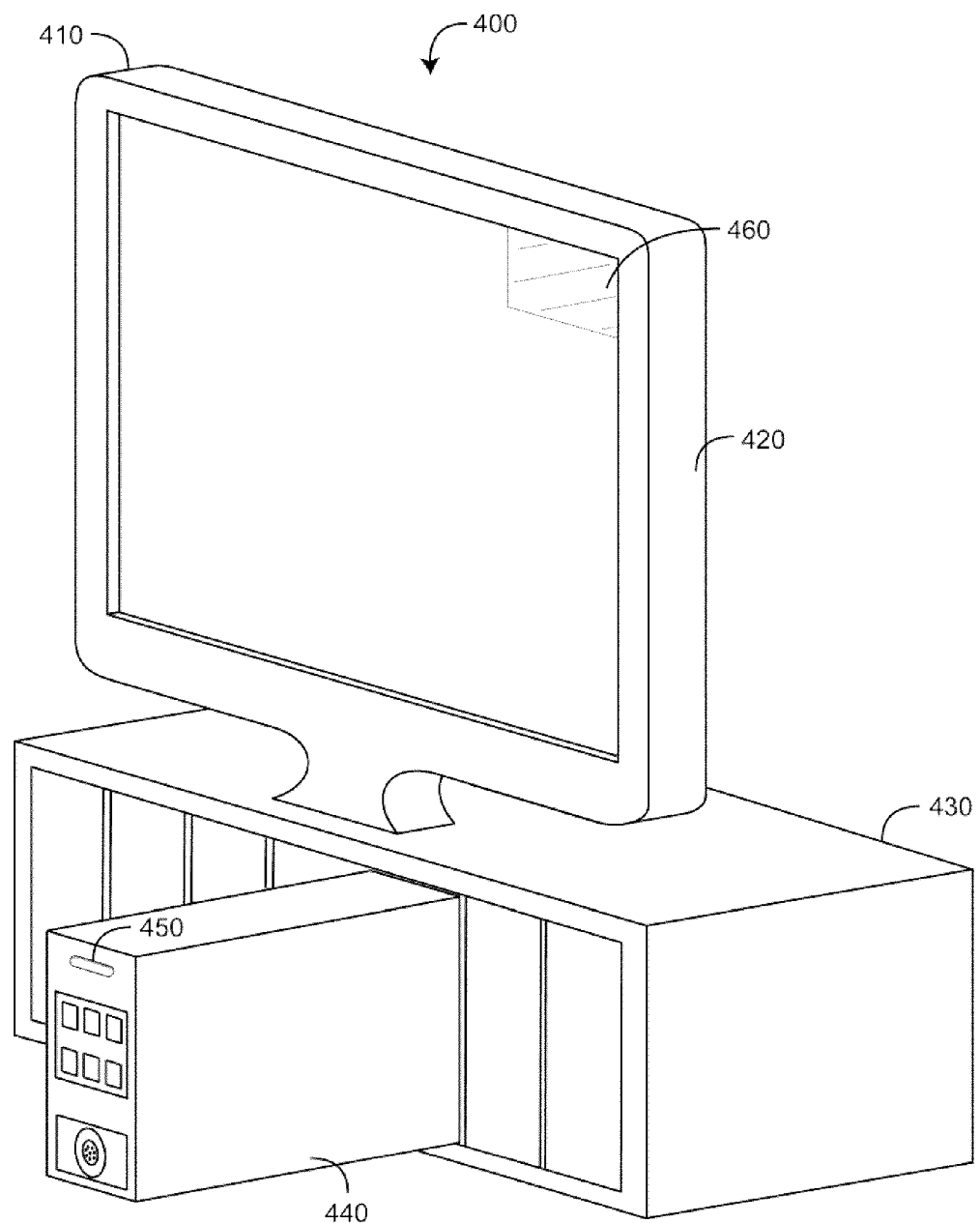
Figure 5:
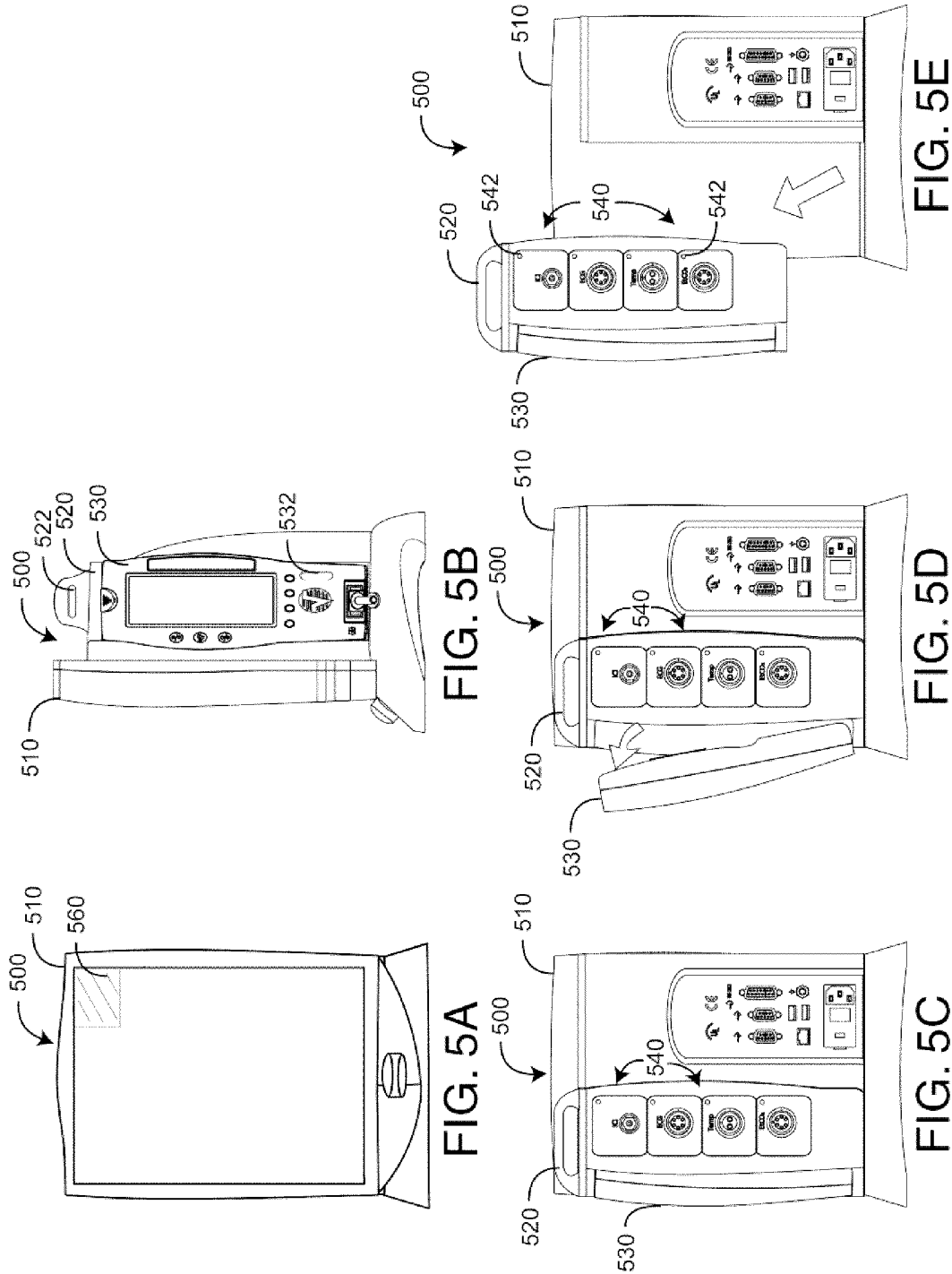

FIG. 4 illustrates a physiological monitoring system 400 comprising a multi-parameter physiological monitoring system (MPMS) 410 and a corresponding plug-in module 440. The MPMS 410 may be capable of measuring a wide range of physiological parameters according to various plug-in modules, such as pulse oximetry, blood pressure, ECG and capnography to name a few. As an example, a MPMS having plug-in modules is described in U.S. Pat. No. 6,770,028 titled Dual Mode Pulse Oximeter, issued Aug. 3, 2004, assigned to Masimo and incorporated by reference herein. A panel light 450 on the plug-in 440 displays a selected color associated with a plug-in profile, such as described with respect to FIG. 1, above. A monitor display 420 also provides a color profile indicator 460 and a corresponding textual description of a current profile. In an embodiment, the display profile indicator 460 simply reflects the configuration profile of the plug-in. In an embodiment, the display profile indicator 460 indicates a pre-programmed MPMS profile that is adopted by the plug-in 440 when plugged into the MPMS, modifying the panel light 450 accordingly. In an embodiment, the MPMS profile is combined with the plug-in profile when docked, modifying both the panel light 450 and the display indicator 460 accordingly. In an embodiment, an MPMS configuration profile is downloaded to the plug-in, as verified by the plug-in profile indicator 450. In this manner, the MPMS 410 functions as a profile defining device for the plug-in 440.

FIGS. 5A-E is a multi-module monitor 500 including a display and docking station 510, a removable shuttle 520, a handheld monitor 530 and plug-ins 540, all having corresponding profile configuration indicators 522, 532, 542. The docking station 510 has a shuttle port that allows the shuttle 520 to dock. The shuttle 520 has a handheld port that allows the handheld monitor 530 to dock. Accordingly, the modular patient monitor 500 has three-in-one functionality including a handheld 530, a handheld 530 docked into a shuttle 520 as a handheld/shuttle and a handheld/shuttle docked into the docking station 510. When docked, the three modules of handheld 530, shuttle 520 and docking station 510 function as one unit. Plug-in modules 540 expand parameter functionality. In an embodiment, the handheld monitor 530 incorporates blood parameter measurement technologies including HbCO, HbMet, $SpO_2$ and Hbt, and the shuttle station 520 incorporates non-blood parameters, such as intelligent cuff inflation (ICI), end-tidal $CO_2$ ($EtCO_2$), acoustic respiration rate (ARR), glucose, patient body temperature (Temp) and ECG, to name a few. A multi-module monitor is described in U.S. Pat. App. Pub. No. 2008/0108884 A1 titled Modular Patient Monitor, filed Sep. 24, 2007 and incorporated by reference herein.

As shown in FIG. 5A-E, the monitor 500 is capable of measuring a wide range of physiological parameters according to a combination of plug-in modules 540, a removable shuttle 520, a removable handheld 530 and a docking station 510. The docking station 510 can display a color profile indicator 560 and a corresponding textual description of a current profile. The shuttle 520 has a color profile indicator 522. The handheld 530 has a color profile indicator 532. Also, the plug-in modules 540 each have individual color profile indicators 542. In an embodiment, the docking station 510 and shuttle 520 simply reflect the configuration profile of what is docked. In an embodiment, a pre-programmed docking station profile is adopted, at least in part, by each layer of docked components, modifying individual profile indicators 522, 532, 542 accordingly. In an embodiment, the docking station 510 profile is combined with one or more of the profiles of each of the docked components 520, 530, 540 when docked, modifying the docking station configuration profile indicator 560 accordingly. In an embodiment, a docking station configuration profile is downloaded to one or more of the docked components 520, 530, 540 as verified by the docked component profile indicators 522, 532, 542. In this manner, the docking station 510 functions as a configuration profile defining or programming device.

Figure 6:
FIG. 6 is a perspective view of a physiological monitoring system responsive to a wall-mounted or a tag-mounted short-range wireless device for selection of a configuration profile.

FIG. 6 illustrates a physiological monitor 100 that is responsive to a wireless device for configuration profile selection. In particular, multiple configuration profiles are pre-defined for the monitor 100, such as described in detail with respect to FIGS. 7-16, below. Advantageously, a fixed wireless device 610 or a mobile wireless device 620 communicates with the monitor 100 so as to select a particular one of the pre-defined configuration profiles. The monitor 100 then activates that profile, i.e. utilizes the profile settings as the monitor default settings, and illuminates the panel light 150 to a color that designates the active profile, as described above. The active profile may also be indicated by a display 170. The wireless device may use any of various short-range wireless technologies, such as RFID (Radio Frequency Identification) or Bluetooth® (Bluetooth SIG) or medium-range wireless technologies, such as Wi-Fi.

In an embodiment, one or more fixed wireless devices, such as a wall-mounted transmitter or transceiver 610 define particular sections inside of a medical care facility according to the wireless device range and coverage. The wireless device(s) 610 within a particular section transmit a unique ID or code to any monitor located within that section. The monitor 100 responds to that code to activate a pre-defined configuration profile associated with that section. For example, one or more wall-mounted wireless devices 610 may be located in each of an ER, ICU or surgical ward, to name a few. A monitor 100 moved to or otherwise located within a particular section, such as an ER, will automatically activate the ER configuration profile and illuminate the panel light 150 with a color indicating the ER configuration, e.g. red. If the same monitor 100 is then moved to the ICU, it will receive an ICU code from a fixed wireless device located in the ICU and will automatically activate the ICU configuration profile and illuminate the panel light 150 with a color indicating the ICU configuration, e.g. yellow.

In another embodiment, a mobile wireless device, such as incorporated within a personal ID badge or tag 620 transmits a unique ID or code associated with a particular medical care provider or group of providers or associated with technical support. In this manner, the appearance of a particular provider, such as a head physician or medical specialist, in proximity to the monitor 100 triggers the monitor to temporarily activate a specific configuration profile suited to that person's needs as long as that person remains in proximity to the monitor. Alternatively, technical support could utilize the tag 620 to quickly change the configuration profile of a particular monitor. The ID badge or tag 620 may also have a button or switch that selectively activates the specific configuration profile when desired. Wireless activation of configuration profiles is described in further detail with respect to FIG. 11, below.

Figure 7:
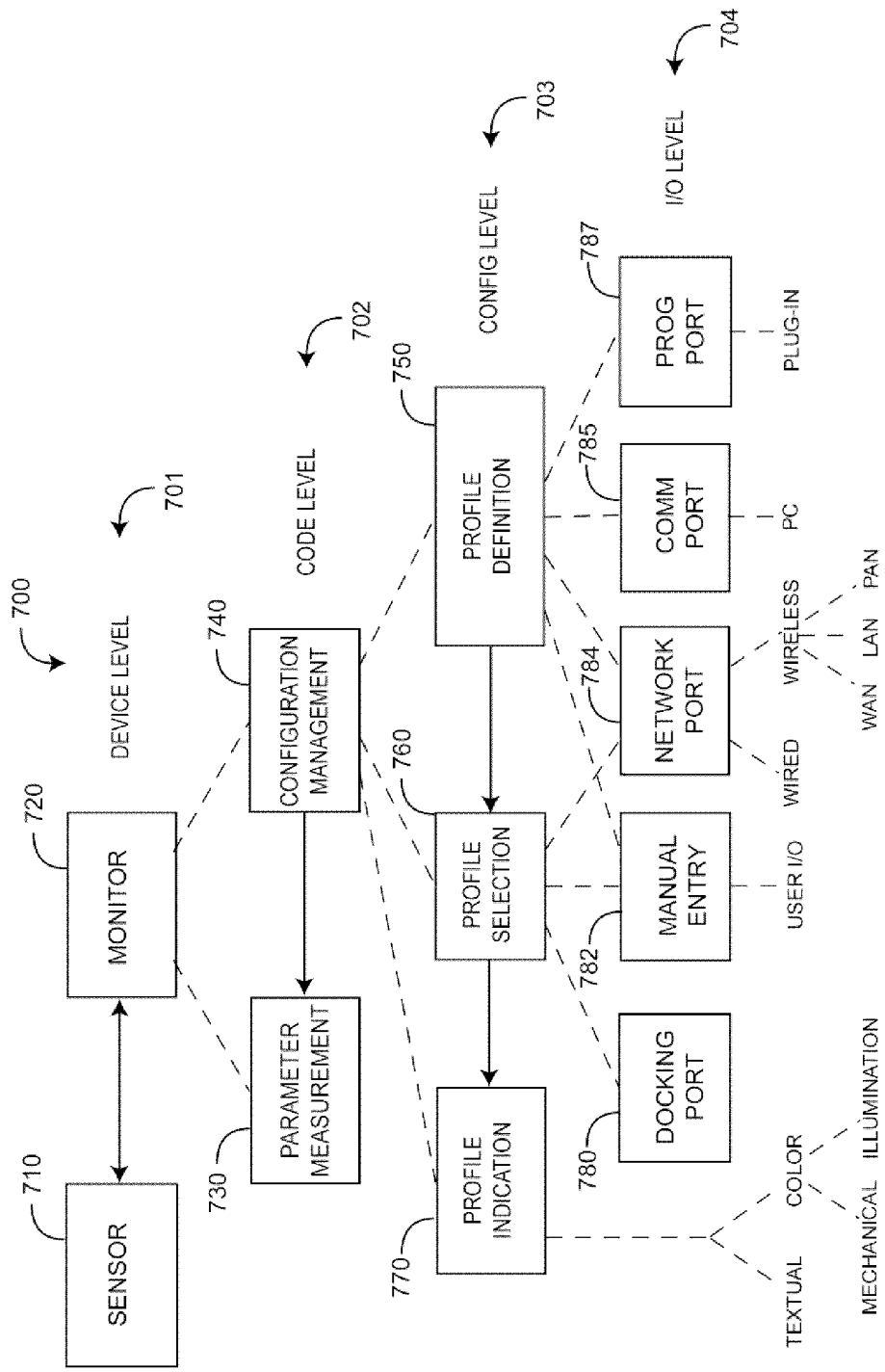
FIG. 7 is a hierarchical block diagram of a monitor configuration system.

FIG. 7 illustrates a monitor configuration system 700 according to a functional hierarchy that includes device 701, code 702, configuration 703 and input/output (I/O) 704 levels. At the device level 701 is a sensor 710 and a monitor 720 having the functional characteristics described with respect to FIG. 1, above. At the code level 702, a monitor has a parameter measurement function 730 and a configuration management function 740 implemented, for example, in code executing on one or more processors within the monitor 720. Parameter measurement 730 involves receiving a sensor signal, processing the sensor signal so as to derive various physiological parameters of interest and displaying the result. Configuration management 740 involves defining one or more configuration profiles 750, selecting one of the defined profiles 760 and indicating the selected profile 770 so that a monitor user can readily determine the default settings that determine the monitor characteristics. Configurable defaults for a patient monitor are described in U.S. Provisional Application Ser. No. 61/126,268 titled Monitor User Interface, which is cited above and incorporated by reference herein.

In particular, a configuration profile is a collection of user-defined default settings for a monitor specifying parameter measurement, display and alarm characteristics, to name a few. In particular, a configuration profile overrides factory defaults at power up. A configuration indicator 770 is a readily visible cue confirming to medical staff that the monitor is operating according to a selected profile 760 or a factory default. In various embodiments, a configuration indicator 770 can be a color or an alphanumeric or both. As described above, a color indicator 770 may be a colored light that illuminates with a user-defined color representing a specific profile 760. A color indicator 770 may also be a colored device, such as a memory, dongle or button plugged into a monitor programming port 787. Also described above, an alphanumeric indicator 770 may be a display of words or numbers that are either descriptive or are recognizable code associated with a selected profile 760.

A monitor's profile definition 750 can be manually entered on front-panel keys (buttons) 782; transferred via short-range wireless technology, such as RFID or wireless personal area network (PAN) 784; defined on a PC and downloaded via communications port 785; programmed into a memory device and transferred to a monitor via a specialized programming port 787; transferred to a monitor via local area network (LAN) or wide area network (WAN) 784, whether wired or wireless or downloaded from a docked device via a docking port 780. A configuration application executing on a PC may interactively prompt a user to define a configuration profile, which is then downloaded to one or more monitors according to any of the methods described above, or with respect to FIGS. 9-10, below.

Figure 8:
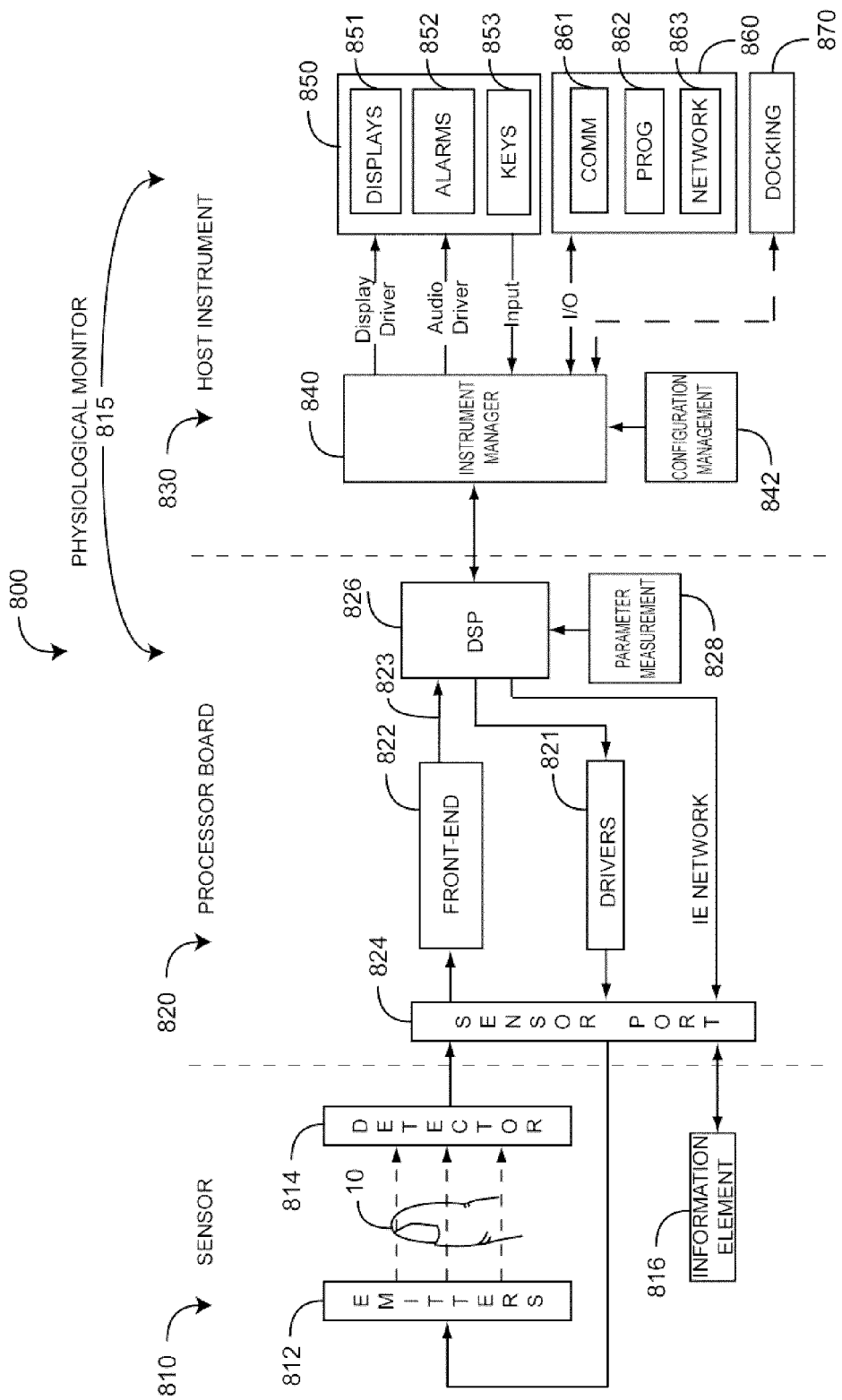
FIG. 8 is a detailed block diagram of a physiological measurement system that utilizes a monitor configuration system.

FIG. 8 illustrates a patient monitoring system 800 including a sensor 810 and a physiological monitor 815 with configuration management features. The sensor 810 is attached to a tissue site, such as a finger 10. The sensor 810 includes a plurality of emitters 812 irradiating the tissue site 10 with multiple wavelengths of light, and one or more detectors 814 capable of detecting the light after attenuation by the tissue 10. The sensor 810 transmits optical radiation at wavelengths other than or including the red and infrared wavelengths utilized in pulse oximeters. The monitor 815 inputs a corresponding sensor signal and is configured to determine the relative concentrations of blood constituents other than or in addition to $HbO_2$ and Hb, such as HbCO, HbMet, fractional oxygen saturation, Hbt and blood glucose to name a few.

The monitor 815 has a processor board 820 and a host instrument 830. The processor board 820 communicates with the sensor 810 to receive one or more intensity signal(s) indicative of one or more physiological parameters. The host instrument 830 communicates with the processor board 820 to receive physiological parameter data calculated by the processor board 820 and to display or otherwise output that data. The host instrument 830 also communicates predetermined settings, described herein as a configuration profile, to the processor board 820. A configuration profile determines, in part, what parameters are displayed and how those parameters are calculated.

As shown in FIG. 8, the processor board 820 comprises drivers 821, a front-end 822, a sensor port 824, a digital signal processor ("DSP") 826 and parameter measurement firmware 828. In general, the drivers 821 convert digital control signals into analog drive signals capable of driving sensor emitters 812. The front-end 822 converts composite analog intensity signal(s) from light sensitive detector(s) 814 into digital data 823 input to the DSP 826. The drivers 821 and front-end 822 are adapted to communicate via the sensor port 824, which is capable of connecting to the sensor 810. In an embodiment, the DSP 826 is adapted to communicate via the sensor port 824 with one or more information elements 816 located on the sensor 810 and one or more cables connecting the sensor 810 to the physiological monitor 815. The processor board 820 may also include one or more microcontrollers in communications with the DSP 826 so as to monitor activity of the DSP 826 and communicate calculated parameters to the host instrument 830. In an embodiment, the processor board 820 comprises processing circuitry arranged on one or more printed circuit boards capable of installation into the monitor 815, or capable of being distributed as some or all of one or more OEM components for a wide variety of host instruments monitoring a wide variety of patient information.

The host instrument 830 includes an instrument manager 840, a user interface 850, I/O ports 860 and in some embodiments a docking port 870. The host instrument 830 displays one or more of a pulse rate, plethysmograph data, perfusion index, signal quality, and values of blood constituents in body tissue, including for example, $SpO_2$, carboxyhemoglobin (HbCO), methemoglobin (HbMet), total hemoglobin (Hbt), fractional oxygen saturation, blood glucose, bilirubin, or the like. The host instrument 830 may also be capable of storing or displaying historical or trending data related to one or more of the measured values or combinations of the measured values.

The instrument manager 840 may be one or more microcontrollers that are in communications with the processor board 820, the user interface 850, the I/O ports 860 and the docking port 870. In particular, the instrument manager 840 inputs calculated parameters and alarm conditions from the processor board 820 and outputs parameter values to the displays 851 and alarm triggers to the user interface 850. Further, the instrument manager 840 responds to user-actuated keys 853 and communicates with external devices via various I/O ports 860. The instrument manager 840 also executes configuration management 842 firmware. Configuration management defines and manages one or more configuration profiles that provide operational settings to the DSP 826 and define user interface characteristics among other functions, as described above with respect to FIG. 7.

Advantageously, the instrument manager 840 communicates with one or more of a user interface 850, I/O ports 860 or a docking port 870 to receive configuration profile data and, in some embodiments, to transmit indications of the default settings. I/O ports 860 may include one or more of a communication port 861, a programming port 862 and a networking port 863. Further, the instrument manager 840 may communicate with an external device removable attached to a docking port 870. In one embodiment, a profile is defined via manually-actuated keys 853 and communicated to the instrument manager 840. In another embodiment, a profile is defined in an external device, such as a PC, and communicated to the instrument manager 840 via a communication port 861, such as a USB or RS-232 interface. In yet another embodiment, a profile is defined in a characterization element having monitor settings stored in memory. The characterization element communicates the defined profile to the instrument manager 840 via a programming I/O port 862. Among other functions, the instrument manager 840 executes configuration management instructions 842 for downloading or otherwise determining one or more user-defined configuration profiles and for indicating the corresponding default settings.

Figure 9:
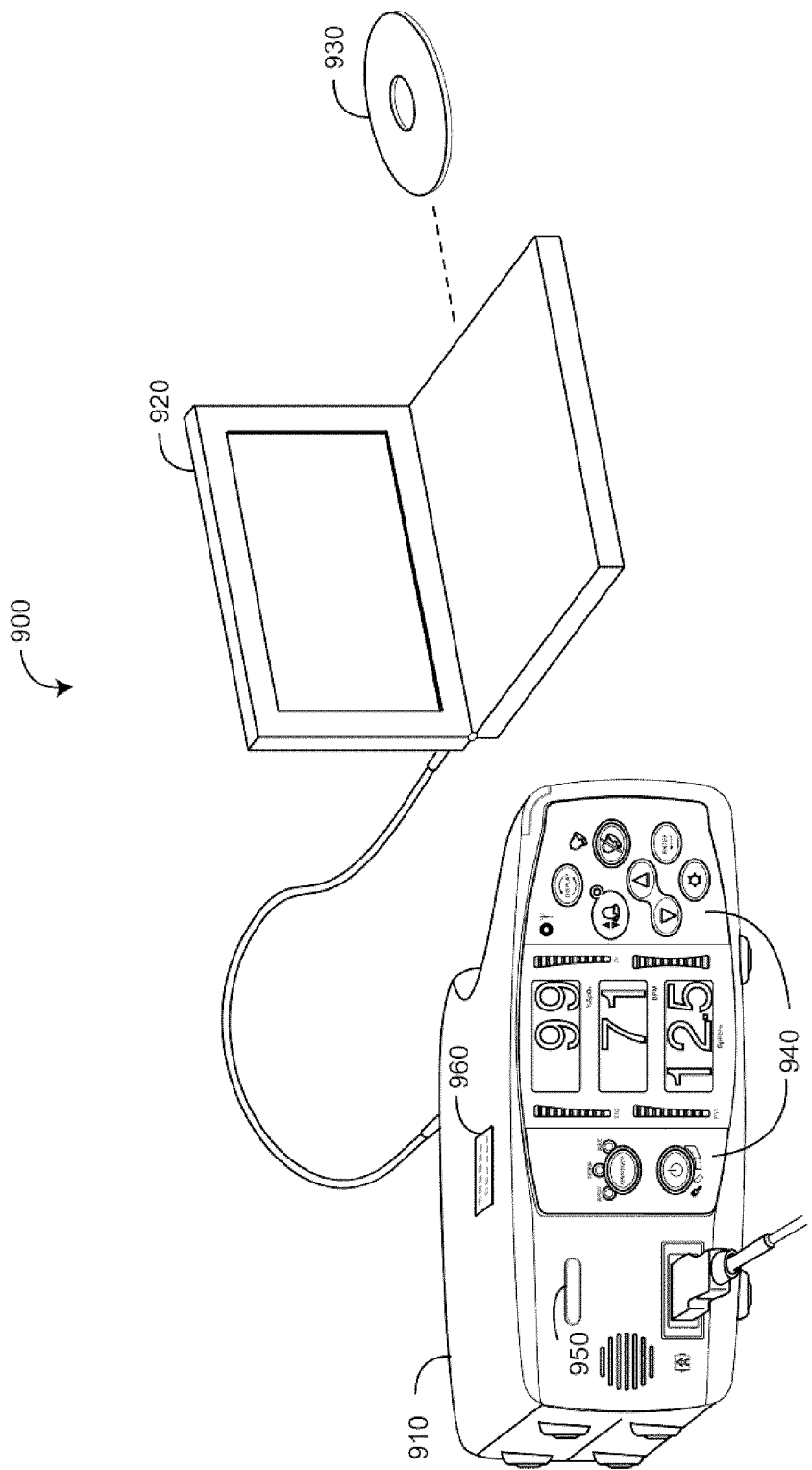
FIG. 9 is a perspective view of a I/O port download embodiment for defining configuration profiles.

FIG. 9 illustrates a profile programming embodiment 900 having a monitor 910 in communications with a PC 920, notebook, PDA or similar device running a configuration application program (AP). The configuration AP, for example, prompts a user through a menu of monitor default setting options. Once a complete set of options is selected, the PC 920 encodes the data as a user-defined profile and downloads the profile as default settings to the monitor 910. Alternatively, a set of predefined configuration profiles may be provided on a CD ROM 930 or similar storage media. A user then simply selects a desired profile via the PC 920, which downloads that profile to the monitor 910.

In other embodiments, a monitor 910 may be factory delivered with a variety of configuration profiles, which are selected via configuration codes, menus or similar cataloging functions using front-panel keys 940. A selected profile is associated with a uniquely colored panel light 950 and/or an identifying alphanumeric on a mini-screen 960 so that medical staff can quickly determine that the appropriate monitor defaults are active upon monitor power-up.

Figure 10:
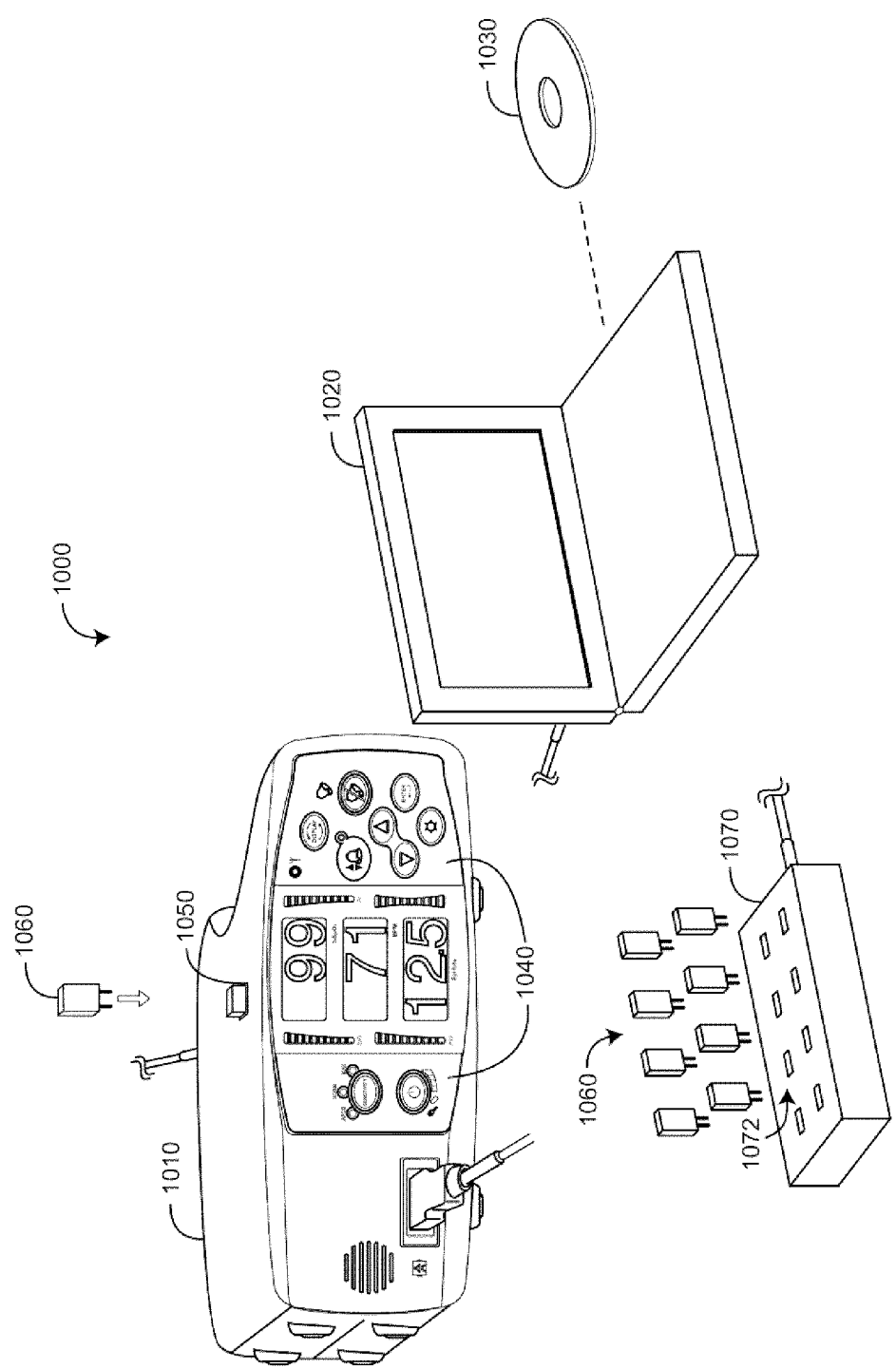
FIG. 10 is a perspective view of a plug-in programming embodiment for defining configuration profiles.

FIG. 10 illustrates another profile programming embodiment 1000 having a monitor 1010 in communications with a characterization element 1060 via a programming port 1050. In this embodiment, a user-defined configuration profile is stored in a colored characterization element 1060, such as an EEPROM, EPROM, PROM or similar non-volatile memory device. The monitor 1010 has a specialized programming or configuration port 1050 that electrically and mechanically accepts and communicates with the memory device 1060. The monitor 1010 reads the characterization element 1060 to determine its default settings upon power-up. The characterization element 1060 is specifically colored so as to provide a readily visible indication of the default profile stored within. The user-defined default profile is easily changed by removing one characterization element 1060 from the port 1050 and replacing it with a differently colored characterization element 1060 selected from a pre-loaded set of memory devices.

Also shown in FIG. 10, a profile programming device 1070 has multiple programming slots 1072 for mass programming profiles into characterization elements 1060. In particular, a profile is either defined directly in the monitor 1010 or communicated from an external device, such as a PC 1020. A profile may be directly programmed in the PC 1020 or loaded from a CD ROM 1030. The PC 1020 communicates with the programming device 1070 to mass-produce characterization elements all having the same profile or each having different profiles depending on the programming slot 1072. In an embodiment, a single characterization element 1060 may be programmed via the monitor 1010 while inserted into the port 1050. The profile programmed may be downloaded to the monitor 1010 from the PC 1020 or entered directly into the monitor 1010 via front-panel keys 1040.

Figure 11:
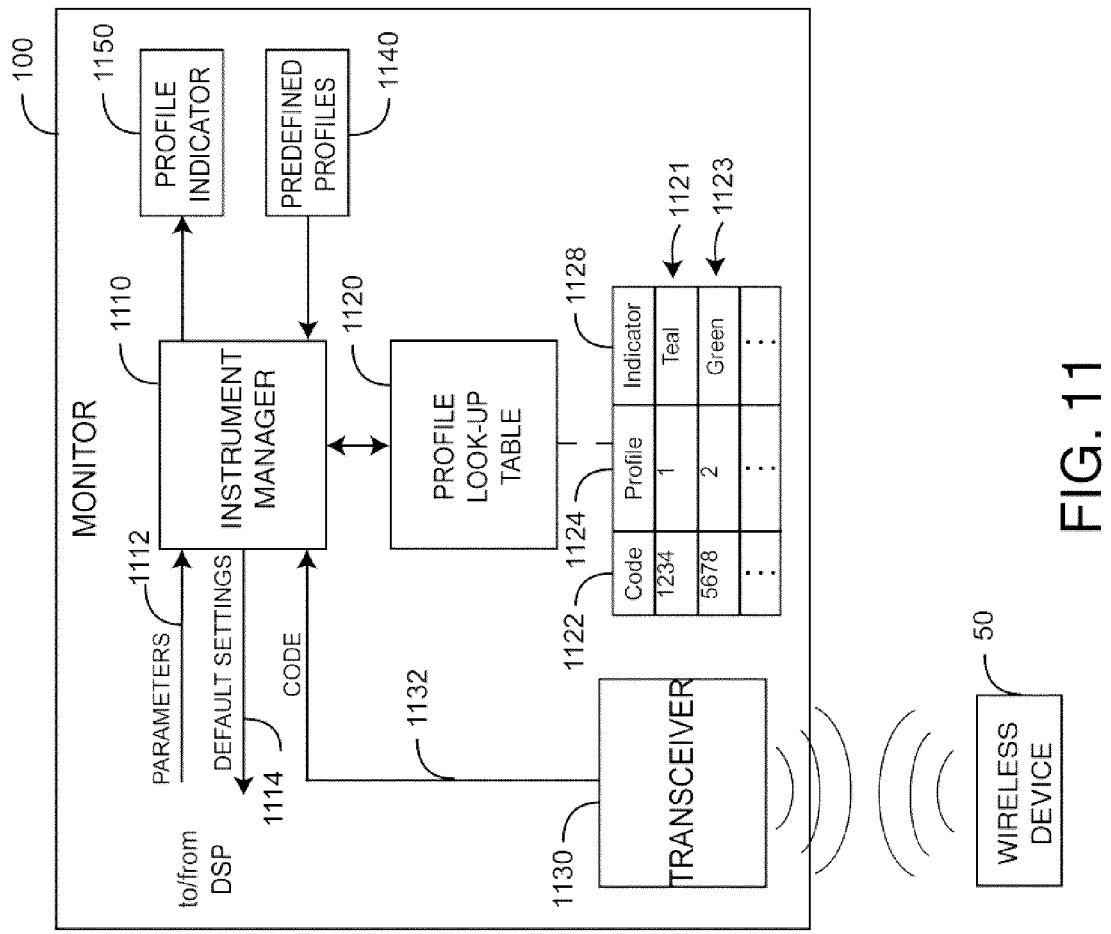
FIG. 11 is a detailed block diagram of a physiological monitoring system responsive to a short-range wireless device for selection of a configuration profile.

FIG. 11 illustrates a physiological monitor 100 that is responsive to a wireless device 50 for configuration profile selection, such as described with respect to FIG. 6, above. The monitor 100 has an instrument manager 1110 that receives calculated physiological parameters 1112 from a digital signal processor (DSP) and provides default settings 1114 to the DSP, such as described with respect to FIG. 8, above. The monitor 1100 has a profile lookup table 1120, a wireless transceiver 1130 or receiver, predefined profiles 1140, and a profile indicator 1150. A wireless device 50 is in communications with the wireless transceiver 1130 when the wireless device 50 is in the vicinity of the monitor 100. The wireless device 50 may be a fixed device, such as a wall-mounted transceiver or transmitter that designates an area within a building or facility, such as described with respect to FIG. 6, above. Alternatively, the wireless device may be a tag or card utilizing short range wireless transceiver or transmitter technology, such as RFID or Bluetooth®.

As shown in FIG. 11, the wireless device 50 transmits a code 1132 to the transceiver 1130 that corresponds to one of the predefined profiles 1140. The transceiver 1130 communicates the profile code 1132 to the instrument manager 1110. The instrument manager 1110 access the lookup table 1120 so as to determine a particular profile corresponding to the code 1124. The instrument manager 1110 loads the selected profile as the monitor default settings and communicates at least some of those settings 1114 to the DSP.

Figure 12A:
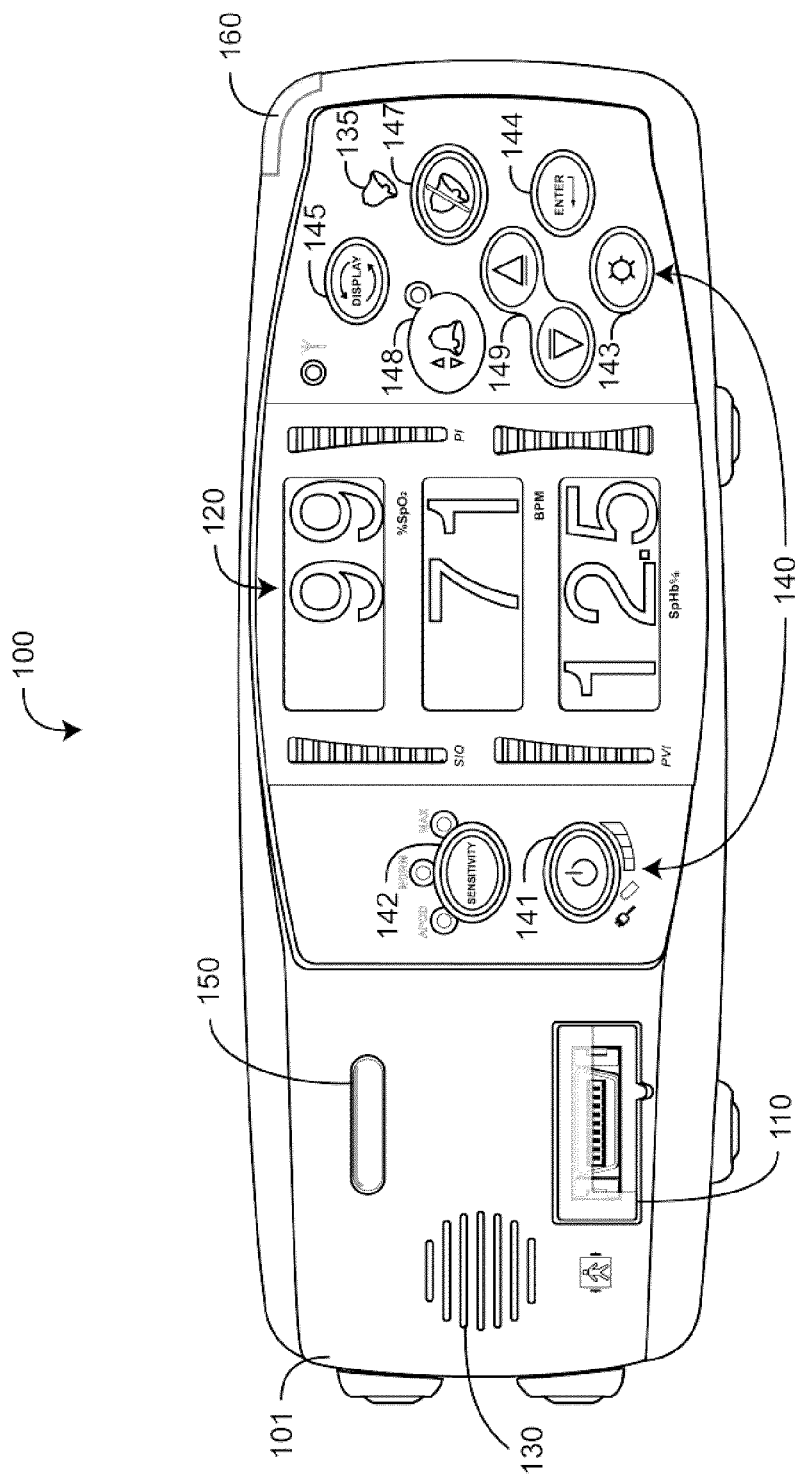
FIGS. 12A-D are front, top and back views, respectively, of a horizontal monitor embodiment and a front view of a vertical monitor embodiment having configuration indicators.
Figure 12B:
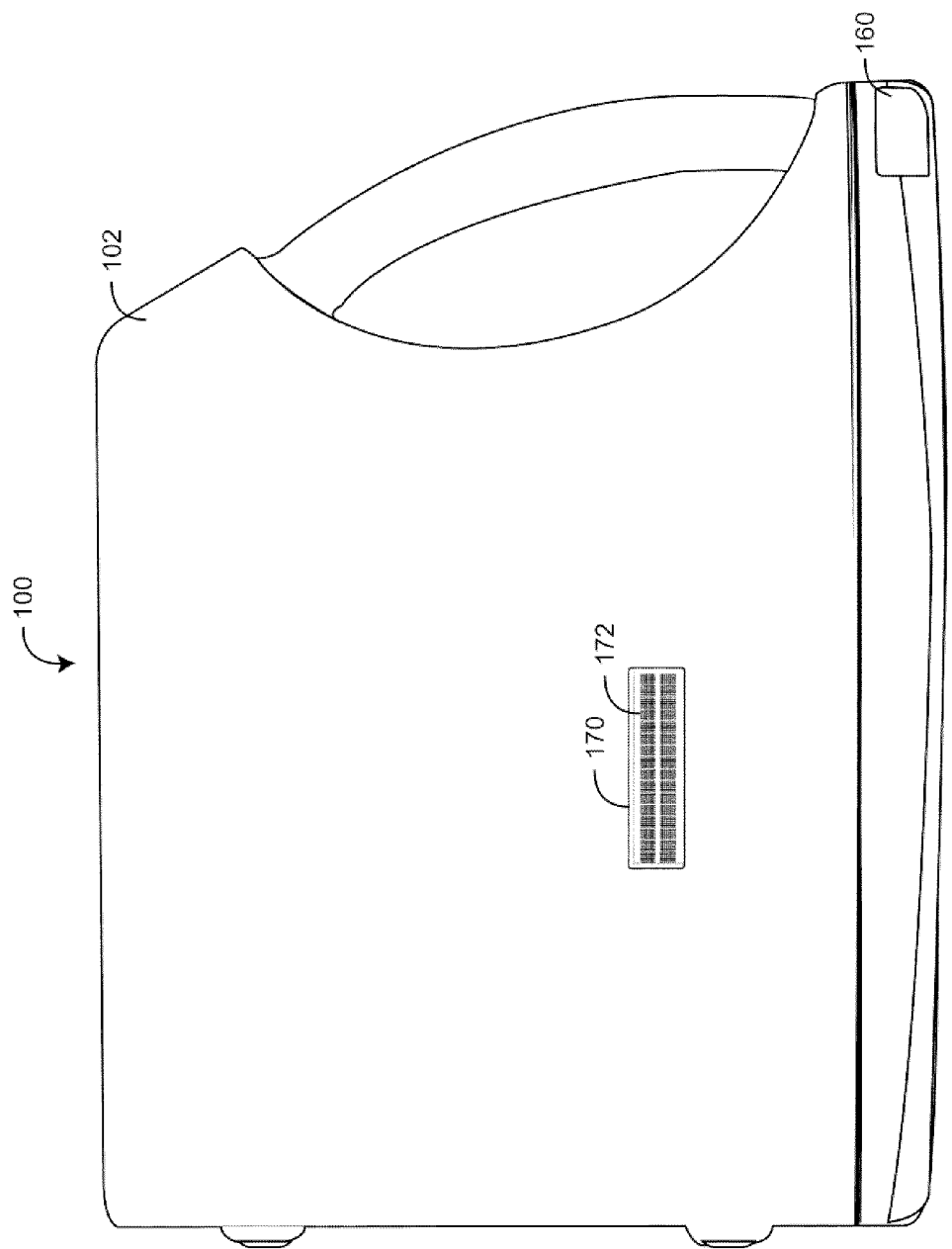
Figure 12C:
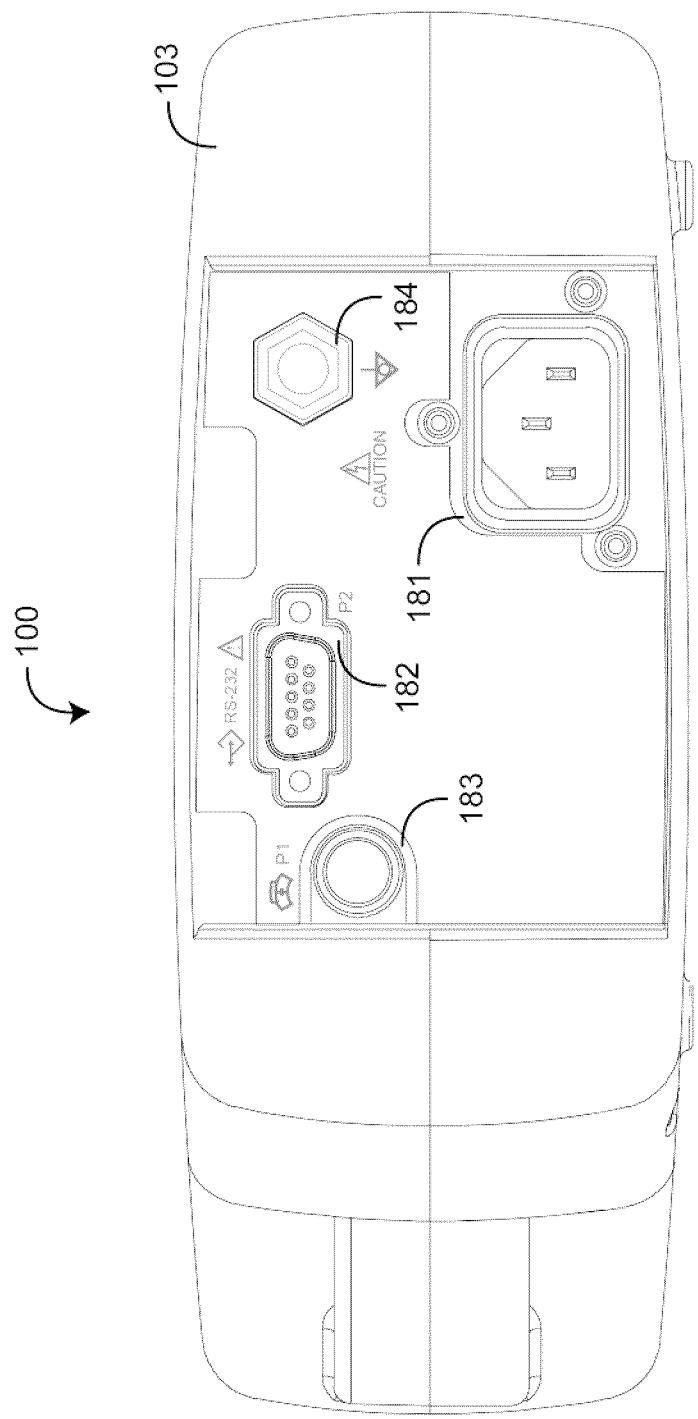
Figure 12D:
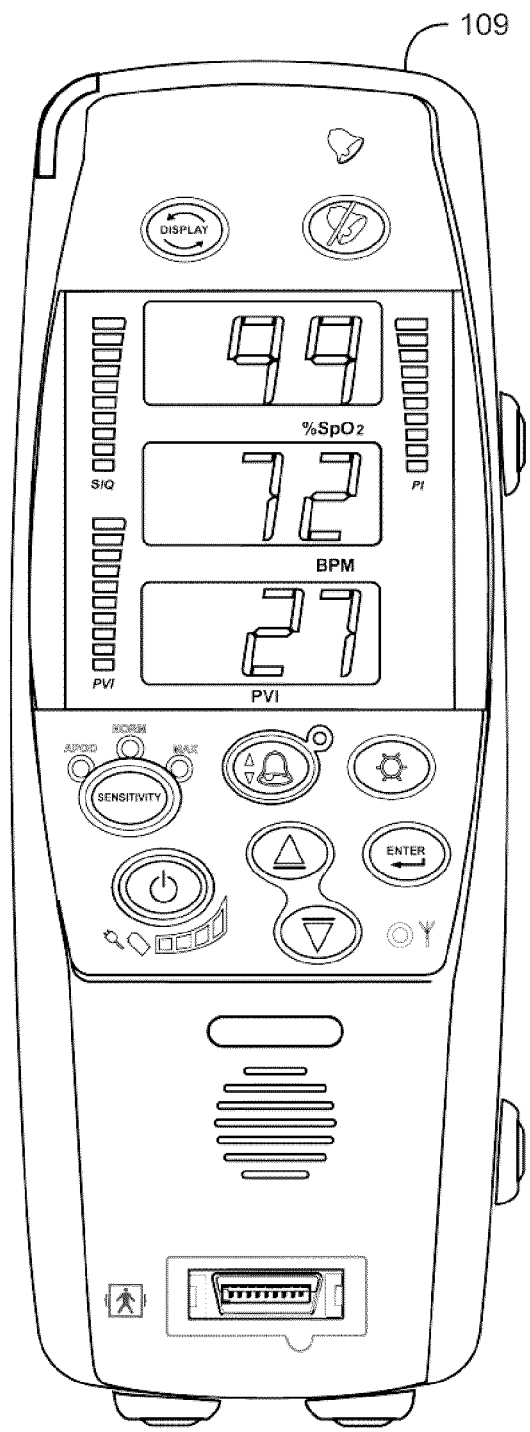

FIGS. 12A-D illustrate further details of a monitor 100 described above with respect to FIG. 1. As shown in FIG. 12A, the monitor front panel 101 has a sensor port 110, parameter displays 120, a speaker 130, control buttons 140, a panel light 150 and a status light 160. The sensor port 110 accepts a patient cable 30 (FIG. 1) connector so as to communicate with a sensor 20 (FIG. 1). The parameter displays 120 provide numerical readouts of measured blood parameters such as oxygen saturation (SpO2), pulse rate (BPM) and total hemoglobin. The speaker 130 provides, for example, an audio indication of alarms. The control buttons 140 provide user control and selection of monitor features including power on/off 141, sensitivity 142, brightness 143, display 145, alarm silence 147 and alarm limits 148 and allow input of a configuration profile via up and down scrolling 149 and enter 144 buttons. An alarm status light 135 indicates high priority alarms. As shown in FIG. 12B, the monitor top panel 102 has an LCD display 170. As shown in FIG. 12C, the monitor back panel 103 provides a power entry module 181, a serial output connector 182, a nurse call connector 183 and a ground connector 184. FIG. 12D illustrates a vertical monitor 109 embodiment of the monitor 100 described with respect to FIG. 1 and FIGS. 12A-C, above.

Figure 13:
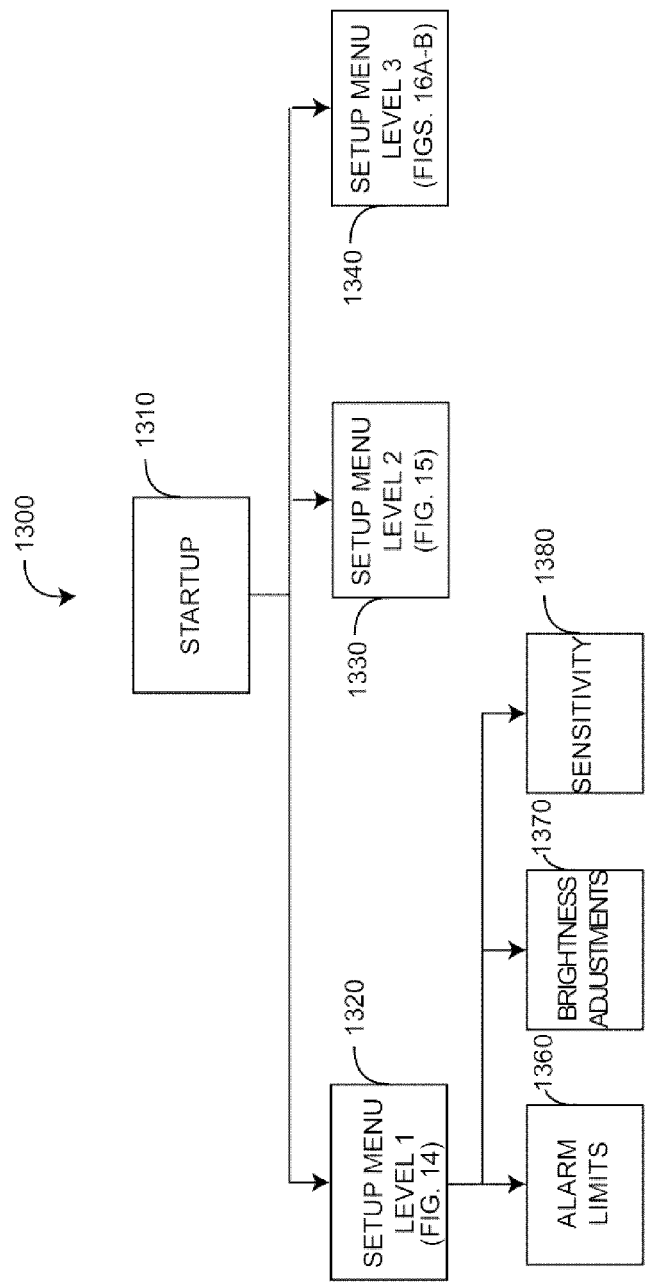
FIG. 13 is a general block diagram illustrating a tri-level configuration user interface, further illustrated in FIGS. 14-16.

FIG. 13 illustrates a tri-level monitor user interface that utilizes front panel buttons (keys) to navigate through the menu selections. Advantageously, monitor settings that are typically adjusted most often for patient monitoring (level 1) are segregated from settings typically adjusted less often (level 2). Level 1 and level 2 settings are further segregated from advanced settings (level 3) that require a timed, combination button press to enter. In particular, this user interface allows a user to manually enter a configuration profile, such as described above, and to associate that profile with a color displayed by the panel light.

As shown in FIG. 13, setup level 1 1320 contains the parameter and measurement settings that are adjusted most often including alarm limits 1360, display brightness 1370, and sensitivity settings 1380. Setup level 2 1330 contains parameter and measurement settings that are not changed as frequently as level 1, including alarm volume, alarm silence, alarm delay, clear trend and button volume parameters.

Setup level 3 1340 contains advanced parameter and measurement settings. Once a menu level is accessed, a front panel button (level 1 only) or the enter button (level 2 and 3) is used to move from one option to the next allowing repeated cycling through the options. The up and down buttons are used to adjust values within each option. The enter button is pressed to set the value.

Figure 14:
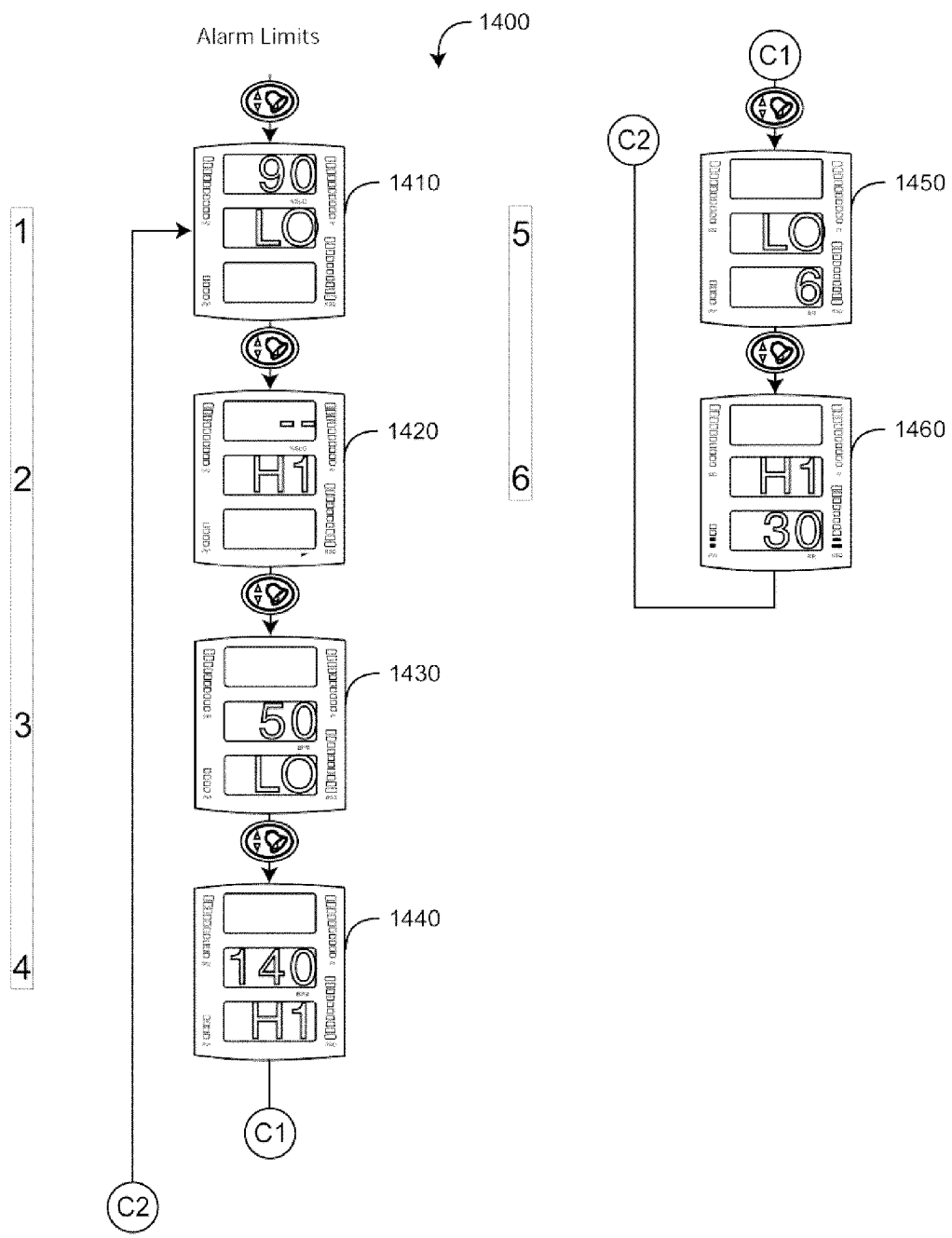
FIG. 14 is a level 1 exemplar flow diagram.

FIG. 14 illustrates a level 1 example for setting alarm limits. The alarm limits button is pressed to access the alarm limits menu. The alarm limits button is used to access the alarm limits options and to move between options of % SpO$_2$ LO 1410, % SpO$_2$ HI 1420, Pulse rate (BPM) LO 1430, Pulse rate (BPM) HI 1440, PVI LO 1450 and PVI HI 1460. Up or down buttons are used to adjust the value to the desired setting. The alarm limits button is pressed to accept the setting and move to the next option. Once the last option is accessed, an additional press of the alarm limits button returns the device to an initial screen. The display button is pressed to exit at any time and return to the initial screen.

Figure 15:
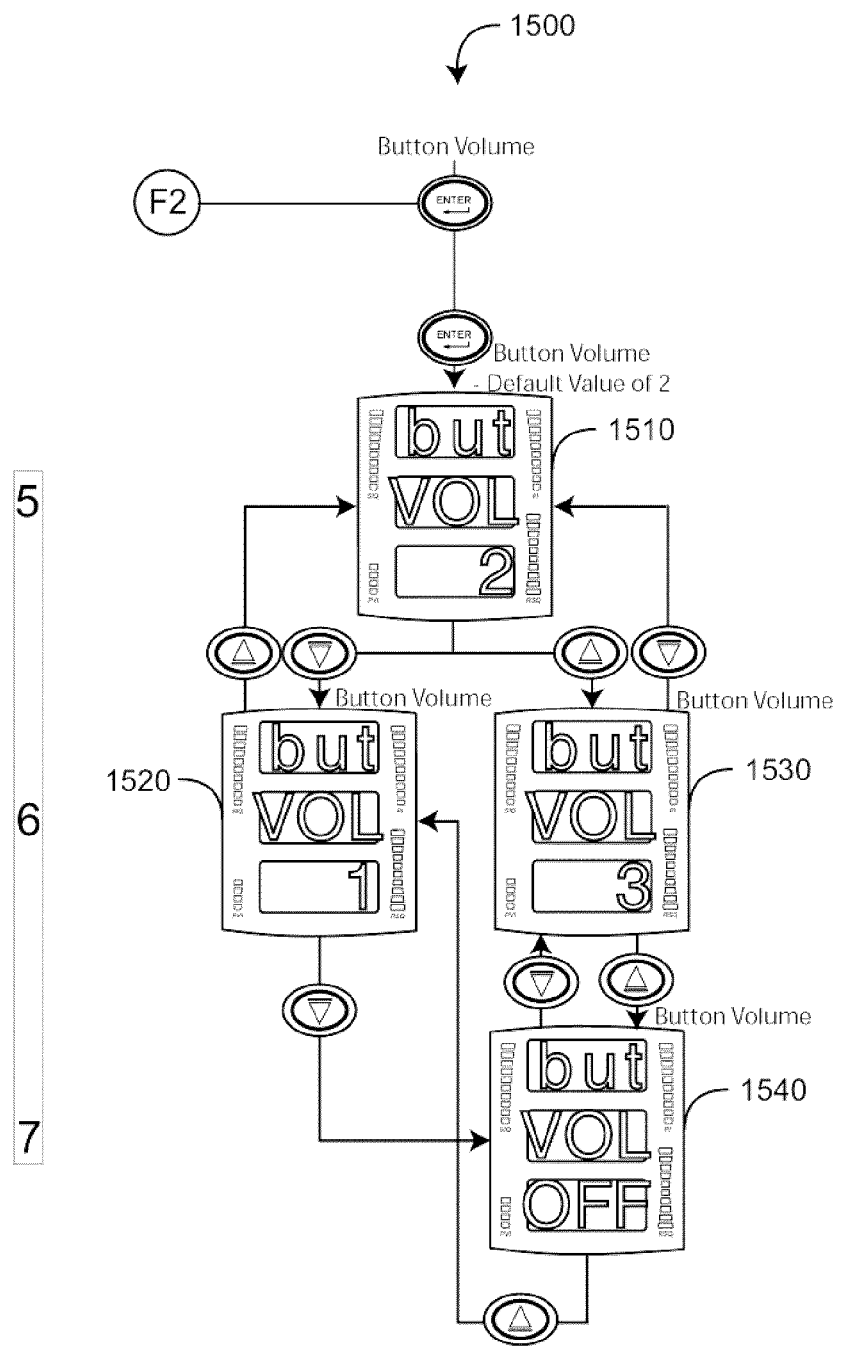
FIG. 15 is a level 2 exemplar flow diagram.

FIG. 15 illustrates a level 2 example for setting button volume. For button volume, the enter button is pressed. The settings options include default level 2 1510, level 1 1520, off 1540 and level 3 1530. Up or down button is used to move between settings and the enter button 1540 is used to accept the setting and move to the next menu screen. The display button is pressed to exit without saving the new setting and to return to the initial display screen.

Figure 16A:
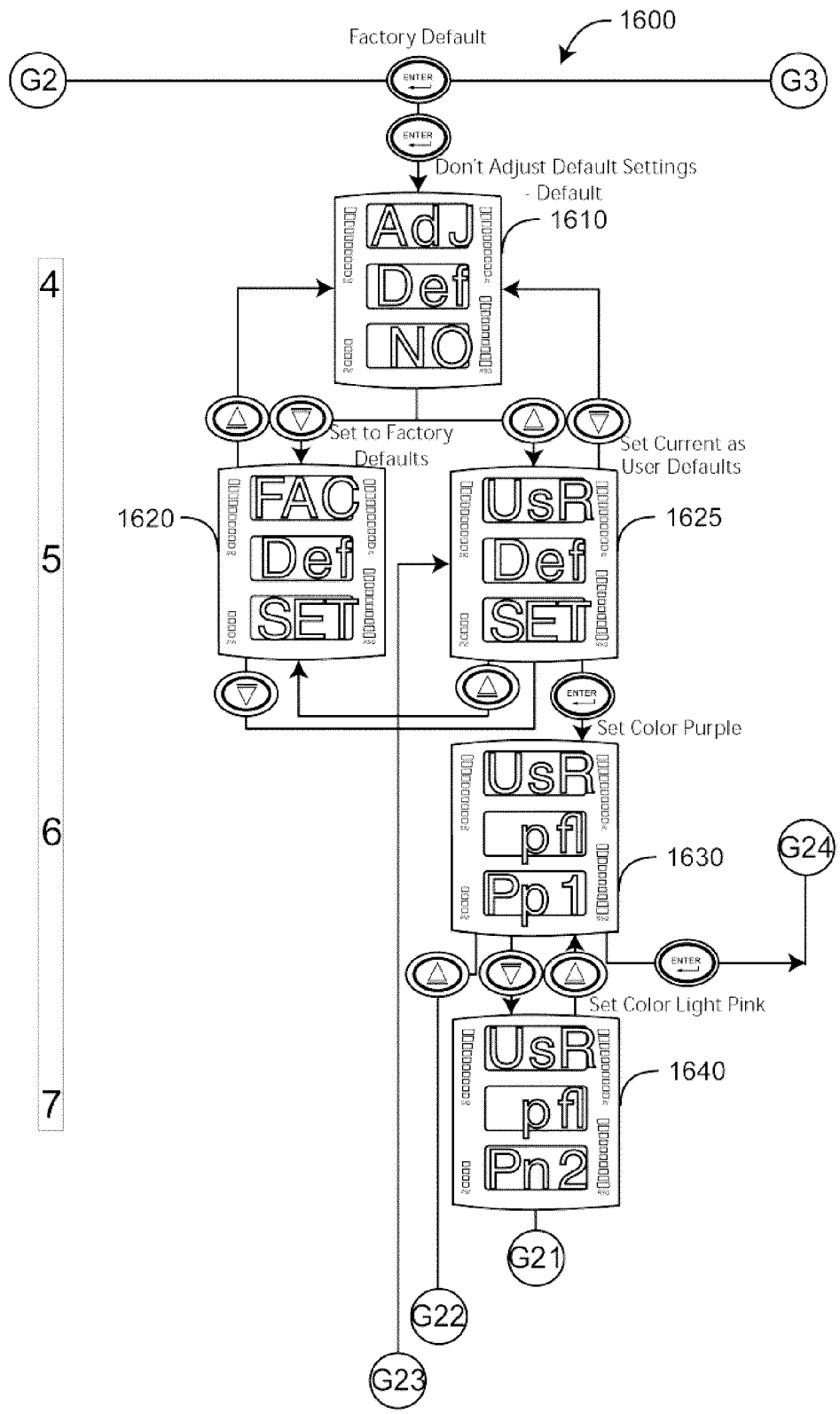
FIGS. 16A-B is a level 3 exemplar flow diagram.
Figure 16B:
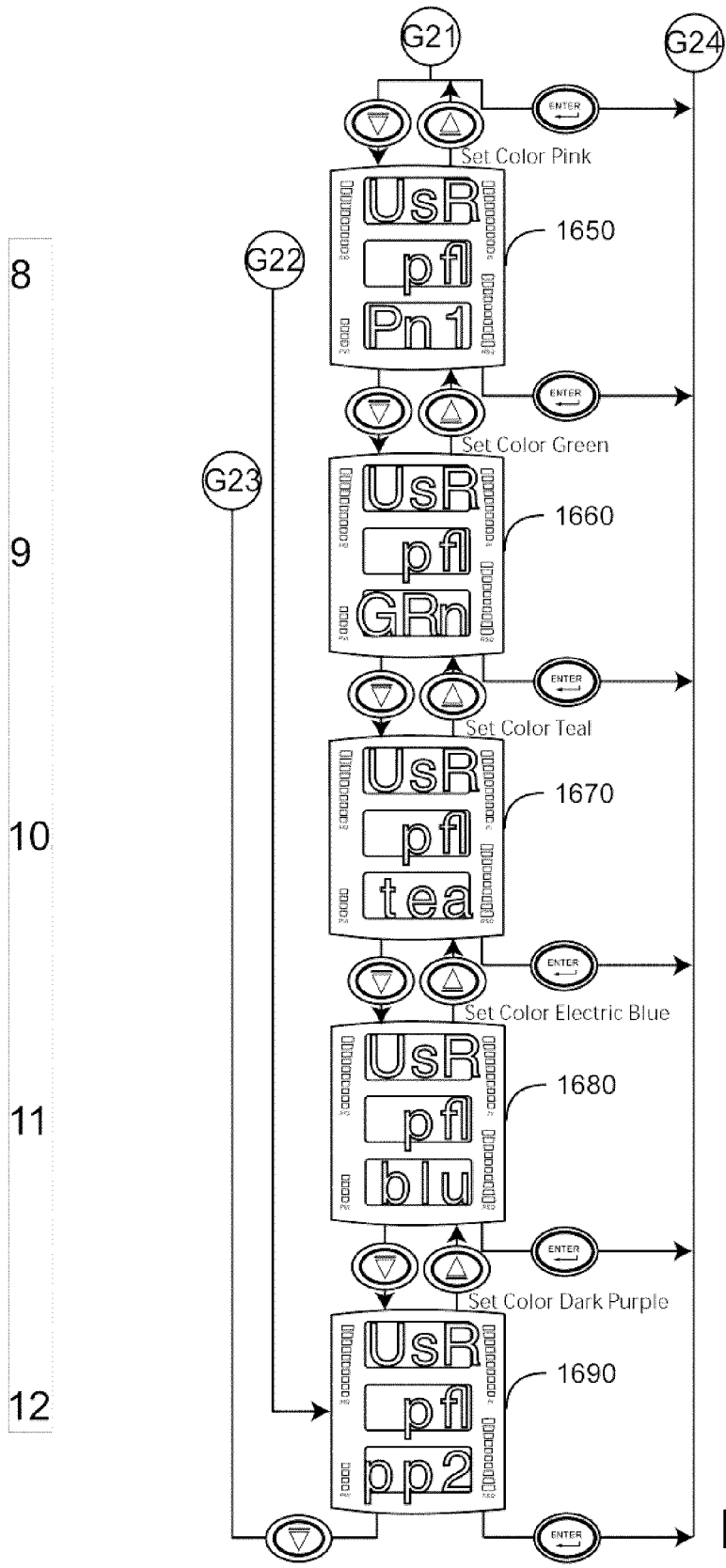

FIGS. 16A-B illustrate a level 3 example for altering the factory defaults. To access level 3 parameters/measurements, the enter button is held down and the down button is pressed for 5 seconds. After entering level 3, the enter button is used to save new settings and move to the next menu. The user may cycle through the menu options by continuing to press the enter button. Pressing the display button exits the menu and returns the display to an initial display screen. The settings options are no change (do not adjust factory default settings) 1610, user default (set to user settings) 1625 and factory default (restore factory default settings) 1620. Up or down button is used to move between settings and the enter button is pressed to accept the setting and move to the next menu. The display button is pressed to exit without saving the new setting and to return to the home display screen. The factory default is set to this setting when configuring a device profile and selecting a color for the device profile LED.

The monitor can be configured to save changes to the device settings as a device profile. Using the button menu or an external configuration application, users can adjust monitor settings and parameter/measurement alarm limits. After changing settings, the user may save the settings as a device profile. This device profile becomes the new default settings and the saved (device profile) settings will be retained after a power cycle. The user may select a color for the device profile LED to associate with the saved profile. The device profile LED will illuminate with the selected color, allowing the user to verify at a glance that a device profile has been set. If changes are made to the device settings after the device profile feature has been enabled, the device profile LED will turn off, indicating a change from the device profile settings. Pressing the Up Arrow once will change the display from the default "Factory Default—Set", to "User Default—Set" (see LCD display) 1610. The user can press the Enter Button again to save the settings, and the monitor will prompt the user to select a color (for the Device Profile LED) to associate with the saved profile. The default color is light blue. On the LCD display, a message alerts the user that light blue is selected, "User Default—light blue". By using the up or down arrows, the user can select from a list of colors 1610-1690. The user selects and saves one color by pressing the Enter Button. The device profile light on the front panel will illuminate with the selected color. When user configured default settings are active, any changes to the default settings cause the device profile LED to turn off until the device is returned to the user configured default settings or powered off.

A monitor configuration system has been disclosed in detail in connection with various embodiments. These embodiments are disclosed by way of examples only and are not to limit the scope of the claims that follow. One of ordinary skill in art will appreciate many variations and modifications.

What is claimed is:

1. A physiological monitor configuration system which provides a single unique colored changeable visual indication to indicate a plurality of user-selected menu settings implemented on the physiological monitor system, the system comprising:

a network interface configured to receive a code when in a vicinity of a wireless device located in a medical care facility, wherein the code is associated with the physical location of the wireless device located in the medical care facility;

a calculation processor that communicates with a physiological sensor configured to obtain an indication of a physiological condition of a patient, the calculation processor configured to calculate a physiological parameter measurement responsive to the indication of the physiological condition obtained by the physiological sensor;

an instrument manager processor in communication with the calculation processor, the instrument manager processor configured to control one or more of a calculation, display and alarm of the monitor configuration system, the instrument manager processor responsive to a configuration profile from a plurality of selectable configuration profiles, each of the plurality of configuration profiles specifying a plurality of user-selected options relevant to a control, display and alarm of the monitor configuration system and each of the plurality of configuration profiles associated with a unique color, wherein the instrument manager processor is configured to automatically select the configuration profile based on the received code from the wireless device located in the medical care facility;

a display configured to display physiological parameter measurements and alarm measurements; and a configuration indicator configured to identify the configuration profile by illuminating a colored visual indication in the unique color associated with the configuration profile, the colored visual indication changeable to indicate which of a plurality of configuration profiles is selected, the configuration indicator separate from the display, wherein the instrument manager processor is configured to turn off the configuration indicator after changes are made to the configuration profile that are different from the plurality of selectable configuration profiles.

2. The monitor configuration system according to claim 1, where the physiological sensor comprises a plurality of emitters that transmit optical radiation into a tissue site and at least one detector that receives the optical radiation after attenuation by pulsatile blood flow within the tissue site.

3. The monitor configuration system according to claim 1 wherein the configuration indicator comprises a panel light.

4. The monitor configuration system according to claim 3 wherein the instrument manager processor is configured to select between a factory-default configuration profile and a user-specified configuration profile.

5. The monitor configuration system according to claim 4 wherein the panel light displays a first color when the factory-default settings are selected and a second color when the user-specified settings are selected.

6. The monitor configuration system according to claim 5 wherein the user-specified settings are manually defined.

7. The monitor configuration system according to claim 6 wherein the panel light color for user-specified settings is manually defined.

8. The monitor configuration system according to claim 3 wherein the panel light displays a first color when a first configuration setting is selected and a second color when a second configuration setting is selected.

* * * * *